(12) United States Patent
Danishefsky et al.

(10) Patent No.: US 9,546,146 B2
(45) Date of Patent: Jan. 17, 2017

(54) MIGRASTATINS AND USES THEREOF

(71) Applicant: Sloan-Kettering Institute for Cancer Research, New York, NY (US)

(72) Inventors: Samuel J. Danishefsky, Englewood, NJ (US); Joan Massague, New York, NY (US); Manuel Valiente Cortes, New York, NY (US); Thordur Oskarsson, Vestmannaeyjar (IS); Malcolm Moore, New York, NY (US); Nicolas Lecomte, New York, NY (US); Ouathek Ouerfelli, Fort Lee, NJ (US); Guangli Yang, Syosset, NY (US)

(73) Assignee: SLOAN-KETTERING INSTITUTE FOR CANCER RESEARCH, New York, NY (US)

( * ) Notice: Subject to any disclaimer, the term of this patent is extended or adjusted under 35 U.S.C. 154(b) by 0 days.

(21) Appl. No.: 15/065,090

(22) Filed: Mar. 9, 2016

(65) Prior Publication Data
US 2016/0221984 A1    Aug. 4, 2016

Related U.S. Application Data

(62) Division of application No. 14/110,115, filed as application No. PCT/US2012/032642 on Apr. 6, 2012, now Pat. No. 9,303,009.

(60) Provisional application No. 61/508,275, filed on Jul. 15, 2011, provisional application No. 61/473,131, filed on Apr. 7, 2011.

(51) Int. Cl.
*A01N 43/02* (2006.01)
*A61K 31/335* (2006.01)
*C07D 313/00* (2006.01)

(52) U.S. Cl.
CPC ........... *C07D 313/00* (2013.01); *A61K 31/335* (2013.01)

(58) Field of Classification Search
None
See application file for complete search history.

(56) References Cited

U.S. PATENT DOCUMENTS

| | | | |
|---|---|---|---|
| 7,943,800 B2 | 5/2011 | Danishefsky et al. | |
| 8,188,141 B2 | 5/2012 | Danishefsky et al. | |
| 8,202,911 B2 | 6/2012 | Huang et al. | |
| 8,324,284 B2 | 12/2012 | Danishefsky et al. | |
| 8,835,693 B2 | 9/2014 | Danishefsky et al. | |
| 8,957,056 B2 | 2/2015 | Danishefsky et al. | |
| 9,303,009 B2 | 4/2016 | Danishefsky et al. | |
| 2007/0037783 A1 | 2/2007 | Huang et al. | |
| 2007/0037852 A1 | 2/2007 | Danishefsky et al. | |
| 2009/0054488 A1 | 2/2009 | Danishefsky et al. | |
| 2009/0124662 A1* | 5/2009 | Danishefsky | A61K 31/365 514/326 |
| 2014/0024705 A1 | 1/2014 | Danishefsky et al. | |

FOREIGN PATENT DOCUMENTS

| | | |
|---|---|---|
| WO | WO-2004/087672 A1 | 10/2004 |
| WO | WO-2004/087673 A2 | 10/2004 |
| WO | WO-2005/019181 A1 | 3/2005 |
| WO | WO-2006/001967 A2 | 1/2006 |
| WO | WO-2006/034478 A2 | 3/2006 |
| WO | WO-2009/070244 A2 | 6/2009 |

OTHER PUBLICATIONS

Anquetin et al., European Journal of Organic Chemistry, 2008, 1953-1958.*
Aubert, C. et al., General method of preparation of trifluoromethyl ketones. Part II. Indirect alkylation of ethyl trifluoroacetylacetate, Journal of Fluorine Chemistry, 44(3):377-94 (1989).
Aubert, C. et al., Methode Generale D'Acces Aux Trifluoromethylcetones. Part I. Direct alkylation of ethyl trifluoroacetylacetate, Journal of Fluorine Chemistry, 44(3):361-76 (1989).
Berge, S.M. et al., Describe pharmaceutically acceptable salts in detail, Journal of Pharmaceutical Sciences, 66(1):1-19 (1977).
Carpenter, A.E. et al., CellProfiler: image analysis software for identifying and quantifying cell phenotypes, Genome Biology 7(10):R100 (2006).
Chambers, A.F. et al., Dissemination and Growth of Cancer Cells in Metastatic Sites, Nat. Rev. Cancer 2:563-572 (2002).
Extended European Search Report for 12768014.8, 6 pages (Sep. 4, 2014).
Gao et al., Rational Design and Characterization of a Rac GTPase-Specific Small Molecule Inhibitor, PNAS 101:20, 7618-7623 (2004).
Gaul, C. et al., The Migrastatin Family: Discovery of Potent Cell Migration Inhibitors by Chemical Synthesis, J. Am. Chem. Soc. 126:(36) 11326-11337 (2004).
International Search Report of PCT/US12/32642, 4 pages (mailed Oct. 2, 2012).
Klein, C. A., Parallel progression of primary tumours and metastases, Nat. Rev. Cancer 9:302-312 (2009).
Lecomte, N. et al., Emergence of potent inhibitors of metastasis in lung cancer via syntheses based on migrastatin, Proceedings of the National Academy of Science, 108(37):15074-15078 (2011).
Madsen, C. D. and Sahai, E., Cancer Dissemination—Lessons from Leukocytes, Development Cell 19:13-26 (2010).
Nakae, K. et al., Migrastatin, A New Inhibitor of Tumor Cell Migration form *Streptomyces* sp. MK929-43F1, Taxanomy, Fermentation, Isolation and Biological Activities, Journal of Antibiotics 53(10):1130-1136 (2000).
Nguyen, D. X. et al., Metastasis: from dissemination to organ-specific colonization, Nat. Rev. Cancer 9:274-284 (2009).
Njardarson, J. T. et al., Discovery of Potent Cell Migration Inhibitors through Total Synthesis: Lessons from Structure-Activity Studies of (+)-Migrastatin, J. Am. Chem. Soc. 126(4):1038-1040 (2004).
Oskarsson et al., Diverted Total Synthesis Leads to the Generation of Promising Cell-Migration Inhibitors for Treatment of Tumor Metastasis: In Vivo and Mechanistic Studies on the Migrastatin Core Ether Analog, J. Am. Chem. Soc., 132:9, 3224-3228, (2010).

(Continued)

*Primary Examiner* — Dennis Heyer
*Assistant Examiner* — Daniel M Podgorski
(74) *Attorney, Agent, or Firm* — Choate, Hall & Stewart LLP; John P. Rearick; Nicholas J. Pace

(57) ABSTRACT

The present invention provides compounds, pharmaceutically acceptable compositions thereof, and methods of using the same.

41 Claims, 14 Drawing Sheets

(56) References Cited

OTHER PUBLICATIONS

Ridley, A. J. et al., Cell Migration: Integrating Signals from Front to Back, Science 302:1704-1709 (2003).
Rodina, A. et al., Selective compounds define Hsp90 as a major inhibitor of apoptosis in small-cell lung cancer, Nature Chemical Biology 3(8):498-507 (2007).
Shan et al., Synthetic Analogues of Migrastatin that Inhibit Tumor Metastasis in Mice, PNAS, 102:10, 3772-3776 (Mar. 8, 2005).
Written Opinion for PCT/US2012/032642, 5 pages (Oct. 2, 2012).
Yilmaz, M. et al., Distinct mechanisms of tumor invasion and metastasis, Trends in Molecular Medicine 13(12):535-541 (2007).
Yilmaz, Mahmut and Christofori, Gerhard, Mechanisms of Motility in Metastasizing Cells, Mol. Cancer Res.; 8(5):629-642 (2010).

\* cited by examiner

C

MIGRASTATINS AND USES THEREOF

CROSS REFERENCE TO RELATED APPLICATIONS

This present application is a divisional of U.S. patent application Ser. No. 14/110,115, filed Oct. 4, 2013 (now U.S. Pat. No. 9,303,009), which is a national phase application under 35 U.S.C. §371 of PCT international application no. PCT/US2012/032642, filed Apr. 6, 2012 which claims priority to U.S. provisional patent application Ser. No. 61/473,131, filed Apr. 7, 2011, and U.S. provisional patent application Ser. No. 61/508,275, filed Jul. 15, 2011, the entire contents of each of which are hereby incorporated by reference.

GOVERNMENT SUPPORT

This invention was made with government support under grant CA103823 awarded by the National Institutes of Health. The government has certain rights in the invention.

BACKGROUND

It is well known that many cancer deaths arise as a consequence of metastatic disease, rather than from the primary tumor. In appreciation of this fact, there is a strong clinical interest in preventing or halting metastasis as a means of treating cancer.

DEFINITIONS

Figure 1:
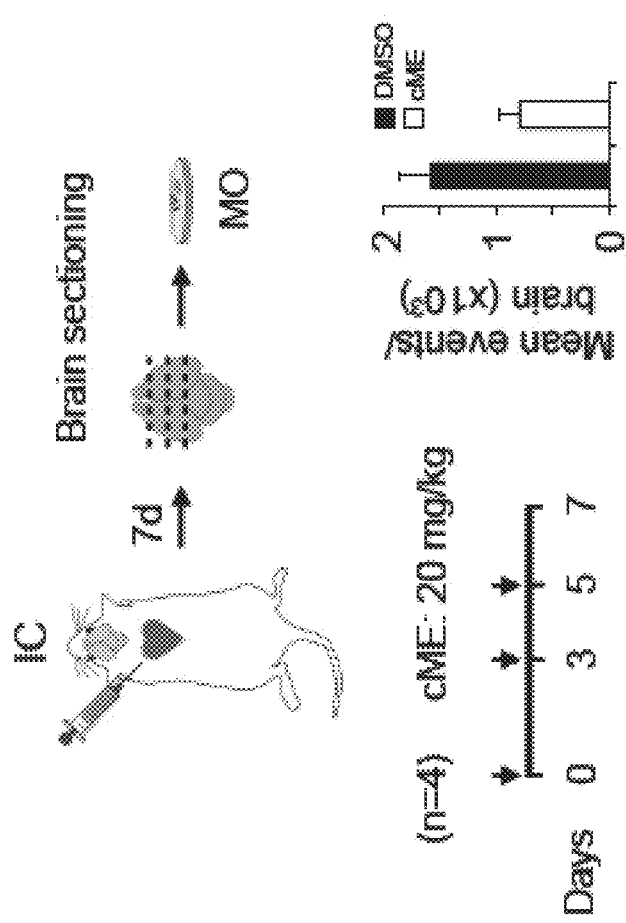
FIG. 1 depicts the experimental protocol and results (bottom right, DMSO left hand bar, cME right hand bar) of the effect of cME on cancer cell migration through the blood brain barrier. Data are average of 4 mice, ±sem.

Certain compounds of the present disclosure, and definitions of specific functional groups are described in more detail below. For purposes of this disclosure, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

As used herein, the following definitions shall apply unless otherwise indicated.

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-12 aliphatic carbon atoms. In some embodiments, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

The terms "cycloaliphatic", "carbocycle", or "carbocyclic", used alone or as part of a larger moiety, refer to a saturated or partially unsaturated cyclic aliphatic monocyclic or polycyclic ring systems, as described herein, having from 3 to 12 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In certain embodiments, the terms "3- to 14-membered carbocycle" and "$C_{3-14}$ carbocycle" refer to a 3- to 8-membered saturated or partially unsaturated monocyclic carbocyclic ring, or a 7- to 14-membered saturated or partially unsaturated polycyclic carbocyclic ring.

As used herein, the term "bivalent saturated or unsaturated, straight or branched, hydrocarbon chain," refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent.

The term "alkynylene" refers to a bivalent alkynyl group. A substituted alkynylene chain is a polymethylene group containing at least one double bond in which one or more hydrogen atoms are replaced with a substituent.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In certain embodiments, alkyl groups contain 1-8 carbon atoms. In certain embodiments, alkyl groups contain 1-6 carbon atoms. In some embodiments, alkyl groups contain 1-5 carbon atoms, in some embodiments, alkyl groups contain 1-4 carbon atoms, in some embodiments alkyl groups contain 1-3 carbon atoms, and in some embodiments alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. Unless otherwise specified, alkenyl groups contain 2-12 carbon atoms. In certain embodiments, alkenyl groups contain 2-8 carbon atoms. In certain embodiments, alkenyl groups contain 2-6 carbon atoms. In some embodiments, alkenyl groups contain 2-5 carbon atoms, in some embodiments, alkenyl groups contain 2-4 carbon atoms, in some embodiments alkenyl groups contain 2-3 carbon atoms, and in some embodiments alkenyl groups contain 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. Unless otherwise specified, alkynyl groups contain 2-12 carbon atoms. In certain embodiments, alkynyl groups contain 2-8 carbon atoms. In certain embodiments, alkynyl groups contain 2-6 carbon atoms. In some embodiments, alkynyl groups contain 2-5 carbon atoms, in some embodiments, alkynyl groups contain 2-4 carbon atoms, in some embodiments alkynyl groups contain 2-3 carbon atoms, and in some embodiments alkynyl groups contain 2 carbon atoms. Representative alkynyl groups include, but are not limited to, ethynyl, 2-propynyl (propargyl), 1-propynyl, and the like.

The term "acyl," used alone or a part of a larger moiety, refers to groups formed by removing a hydroxy group from a carboxylic acid. Non-limiting exemplary acyl groups include carboxylic acids, esters, amides, and carbamates.

The term "halogen" means F, Cl, Br, or I.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenantriidinyl, or tetrahydronaphthyl, and the like. In certain embodiments, the term "6- to 10-membered aryl" refer to a phenyl or an 8- to 10-membered polycyclic aryl ring.

The terms "heteroaryl" and "heteroar-", used alone or as part of a larger moiety, e.g., "heteroaralkyl", or "heteroaralkoxy", refer to groups having 5 to 14 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted. In certain embodiments, the term "5- to 12-membered heteroaryl" refers to a 5- to 6-membered heteroaryl ring having 1 to 3 heteroatoms independently selected from nitrogen, oxygen, or sulfur, or an 8- to 12-membered bicyclic heteroaryl ring having 1 to 4 heteroatoms independently selected from nitrogen, oxygen, or sulfur.

The term "heteroaliphatic," as used herein, means aliphatic groups wherein one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "hetercyclyl," "heterocycloaliphatic," or "heterocyclic" groups.

As used herein, the terms "heterocycle", "heterocyclyl", "heterocyclic radical", and "heterocyclic ring" are used interchangeably and refer to a stable 5- to 7-membered monocyclic or 7-14-membered polycyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). In some embodiments, the term "3- to 7-membered heterocyclic" refers to a 3- to 7-membered saturated or partially unsaturated monocyclic heterocyclic ring having 1 to 2 heteroatoms independently selected from nitrogen, oxygen, or sulfur. In some embodiments, the term "3- to 12-membered heterocyclic" refers to a 3- to 8-membered saturated or partially unsaturated monocyclic heterocyclic ring having 1 to 2 heteroatoms independently selected from nitrogen, oxygen, or sulfur, or a 7- to 12-membered saturated or partially unsaturated polycyclic heterocyclic ring having 1-3 heteroatoms independently selected from nitrogen, oxygen, or sulfur.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

In another aspect, the present disclosure provides "pharmaceutically acceptable" compositions, which comprise a therapeutically effective amount of one or more of the compounds described herein, formulated together with one or more pharmaceutically acceptable carriers (additives) and/or diluents. As described in detail, the pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Unless otherwise stated, structures depicted herein are also meant to include all isomeric (e.g., enantiomeric, diastereomeric, and geometric (or conformational)) forms of the structure; for example, the R and S configurations for each stereocenter, Z and E double bond isomers, and Z and E conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure.

Provided compounds may comprise one or more saccharide moieties. Unless otherwise specified, both D- and L-configurations, and mixtures thereof, are within the scope of the disclosure. Unless otherwise specified, both α- and β-linked embodiments, and mixtures thereof, are contemplated by the present disclosure.

If, for instance, a particular enantiomer of a compound of the present disclosure is desired, it may be prepared by asymmetric synthesis, chiral chromatography, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this disclosure. Such compounds are useful, for example, as analytical tools, as probes in biological assays, or as therapeutic agents in accordance with the present disclosure.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. In preferred embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethyl silyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethyl silylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2, 5-dimethylpyrrole, N-1,1,4,4-tetramethyldisilylazacyclopentane adduct (STABASE), 5-substituted 1,3-dimethyl-1, 3,5-triazacyclohexan-2-one, 5-substituted 1,3-dibenzyl-1,3, 5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present disclosure is not intended to be limited to these protecting groups; rather, a variety of additional equivalent protecting groups can be readily identified using the above criteria and utilized in the method of the present disclosure. Additionally, a variety of protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O$(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$;

—(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6-membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R●, -(haloR●), —(CH$_2$)$_{0-2}$OH, —(CH$_2$)O$_2$OR●, —(CH$_2$)$_{0-2}$CH(OR●)$_2$; —O(haloR●), —CN, —N$_3$, —(CH$_2$)$_{0-2}$C(O)R●, —(CH$_2$)$_{0-2}$C(O)OH, —(CH$_2$)$_{0-2}$C(O)OR●, —(CH$_2$)$_{0-2}$SR●, —(CH$_2$)$_{0-2}$SH, —(CH$_2$)$_{0-2}$NH$_2$, —(CH$_2$)$_{0-2}$NHR●, —(CH$_2$)$_{0-2}$NR●$_2$, —NO$_2$, —SiR●$_3$, —OSiR●$_3$, —C(O)SR●, —(C$_{1-4}$ straight or branched alkylene)C(O)OR●, or —SSR● wherein each R● is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

When used as a chemical bond, "∼∼∼" shall be understood to depict a single carbon-carbon bond with undefined stereochemistry at a carbon center. Thus, a substituent attached to a carbon atom with a "∼∼∼" bond refers to embodiments where the substituent is coming out of the plane of the paper, embodiments where the substituent is going behind the plane of the paper, and combinations (i.e., stereochemical mixtures) thereof. A "∼∼∼" attached to a double bond refers to both the Z and E isomers.

As used herein and in the claims, the singular forms "a", "an", and "the" include the plural reference unless the context clearly indicates otherwise. Thus, for example, a reference to "a compound" includes a plurality of such compounds.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "palliative" refers to treatment that is focused on the relief of symptoms of a disease and/or side effects of a therapeutic regimen, but is not curative.

As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

The expression "unit dose" as used herein refers to a physically discrete unit of a formulation appropriate for a subject to be treated. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. A particular unit dose may or may not contain a therapeutically effective amount of a therapeutic agent.

An individual who is "suffering from" a disease, disorder, and/or condition has been diagnosed with and/or displays one or more symptoms of the disease, disorder, and/or condition.

An individual who is "susceptible to" a disease, disorder, and/or condition has not been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

DETAILED DESCRIPTION OF CERTAIN EMBODIMENTS

The present invention encompasses the recognition that there remains a need for chemotherapeutic compounds that are useful in the treatment of cancer and/or effective at inhibiting cancer metastasis.

The present invention provides, among other things, novel compounds for use in the treatment of cancer. In certain embodiments, such compounds are characterized by having a particularly advantageous pharmacological profile. In some embodiments, such compounds possess increased potency over known migrastatin analogs. In some embodiments, such compounds possess increased solubility over known migrastatin analogs. In some embodiments, such compounds possess increased cancer selectivity over known migrastatin analogs.

The present invention provides, among other things, novel compounds for use in inhibiting cancer metastasis. In certain embodiments, such compounds are useful for inhibiting metastasis of cancers of the lung or breast. In certain embodiments, such compounds are useful for inhibiting metastasis of multiple myeloma. The present invention further provides new and/or improved methods of treating cancer. In certain embodiments, such methods are useful for treating metastatic spread of lung or breast cancers. In certain embodiments, such methods are useful for treating metastatic spread of multiple myeloma. In certain embodiments, such methods are useful for treating metastatic spread of lung or breast cancers to the brain. The present invention further provides new/and or improved methods of inhibiting cancer metastasis. In certain embodiments, such methods are useful for treating cancers of the lung or breast. In certain embodiments, such methods are useful for treating multiple myeloma.

The macrolide migrastatin is a natural product originally isolated from a cultured broth of Streptomyces sp MK929-43F1, as part of screen for microbial products that inhibit cancer cell migration (Nakae, K., Yoshimoto, Y., Sawa, T., Homma, Y., Hamada, M., Takeuchi, T., and Imoto, M. (2000), J Antibiot (Tokyo) 53, 1130-1136). Migrastatin and related synthetic analogs have subsequently been demonstrated to act as inhibitors of migration in other tumor cells, including those of breast, prostate and colon cancer, as well as in vivo, preventing the metastasis of human mammary carcinoma cells to the lung, in mice, by 91-99% (Shan, D., Chen, L., Njardarson, J. T., Gaul, C., Ma, X., Danishefsky, S. J., and Huang, X. Y. (2005), Proc Natl Acad Sci USA 102, 3772-3776). A salient property of migrastastins is the ability to halt migration of tumor cells specifically, but not that of normal cells such as epithelial cells, fibroblasts or leukocytes. Furthermore, at high uM concentrations, migrastatin inhibits the migration of tumor cells in classic wound-healing and chamber cell migration assays yet exhibits minimal cytotoxicity and little or no interference with DNA, RNA and protein biosynthesis (Gaul, C., Njardarson, J. T., Shan, D., Dorn, D. C., Wu, K. D., Tong, W. P., Huang, X. Y., Moore, M. A., and Danishefsky, S. J. (2004), J Am Chem Soc 126, 11326-11337; Njardarson, J. T., Gaul, C., Shan, D., Huang, X. Y., and Danishefsky, S. J. (2004), J Am Chem Soc 126, 1038-1040).

Since the initial discovery of the natural migrastatin compound, Applicant has developed strategies for the total synthesis of migrastatin, as well as simplified synthetic routes to produce migrastatin analogs, several of which inhibit tumor cell migration by up to three orders of magnitude compared to the natural macrolide. Although several synthetic migrastatin analogs have been developed in recent years, as described above, and in other references described herein, there remains a need for further investigation to develop novel chemotherapeutics capable of an improved pharmacological profile.

In some embodiments, provided compounds and/or methods are useful in medicine. In some embodiments, provided compounds and/or methods are useful in the treatment of cancer. In some embodiments, provided compounds and/or methods are useful in the treatment of solid tumors. In some embodiments, provided compounds and/or methods are useful in the treatment of tumors of epithelial origin. In some embodiments, provided materials and/or methods are useful in the treatment of breast cancer or lung cancer.

Cancer metastasis is generally regarded as a multi-step process whereby uncontrolled cell proliferation is followed, or accompanied, by local invasion and angiogenesis, entry and survival in the circulatory system, extravasation, and finally, establishment of distant tumors in secondary organs (Nguyen, D. X., Bos, P. D., and Massague, J. (2009), Nat Rev Cancer 9, 274-284; Chambers, A. F., Groom, A. C., and MacDonald, I. C. (2002), Nat Rev Cancer 2, 563-572; Klein, C. A. (2009), Nat Rev Cancer 9, 302-312). Interference at one or several of these points could potentially block metastasis, whether by assisting in managing the primary tumor in conjunction with other therapies, or by preventing the formation or spread of new tumors after surgery and other systemic treatments. The regulation of cell migration during metastasis is relatively unexplained compared to other events, such as angiogenesis, but parallels may be drawn from migration mechanisms used by cells of the immune system, or during embryonic development (Madsen, C. D., and Sahai, E. (2010), Dev Cell 19, 13-26; Yilmaz, M., and Christofori, G. (2010), Mol Cancer Res 8, 629-642). At various points in the migratory process, cancer cells break through cell barriers, whether it is at the basement membrane, blood vessels, lymphatic system or target organ. To do so, epithelial mesenchymal transition (EMT), alterations in cell adhesion, actin dynamics, proteolytic activity, and chemokine receptivity are engaged over the course of migration. Notably, metastatic cancer cells may migrate as solitary cells, as in colorectal cancer for example, or collectively, as is the principal form of invasion by squamous cell carcinoma.

Based on studies in highly metastatic 4T1 breast cancer cells, the cellular basis of macroketone and macrolactam cell migration interference appears be one that is directed at lamellipodia formation, in a Rac GTPase-dependent manner. Lamellipodia are actin-driven projections on the leading edge of mobile cells, and is possibly responsible for pulling the cell forward during migration. Rac is one of three Rho GTPases required for lamellipodia protrusion, and stimulates the downstream effector proteins Arp2/3 to induce dendritic actin polymerization (Ridley, A. J., Schwartz, M. A., Burridge, K., Firtel, R. A., Ginsberg, M. H., Borisy, G., Parsons, J. T., and Horwitz, A. R. (2003), Science 302, 1704-1709). Through a variety of molecular feedback pathways, Rac also acts to reinforce cell polarity by defining the leading edge of a migrating cell. Notably, Rac is elevated in 4T1 breast cancer cells suggesting that, in these transformed cells at least, without wishing to be bound by any particular theory, this may be a possible mechanism by which migrastatin targets metastasis-specific migration while sparing normal cells. Recent studies show that migrastatin ether (depicted below), the simplest analog, produces in vitro and in mouse models similar effects against transformed breast cancer cells, suggesting a possible link to actin-bundling.

Applicant's own work on the synthesis of new migrastatins for cancer therapeutics has yielded promising results. Specifically, migrastatin analogs known as core macroketone, core macrolactam and migrastatin ether have been selected for pre-clinical studies and exhibit significant potential as cancer cell migration inhibitors (Oskarsson, T., Nagorny, P., Krauss, I. J., Perez, L., Mandal, M., Yang, G., Ouerfelli, O., Xiao, D., Moore, M. A., Massague, J., and Danishefsky, S. J. (2010), J Am Chem Soc 132, 3224-3228).

Prior to the present disclosure, diverted chemical synthesis has delivered on its promise for the increase of activity while insuring low to nonexistent toxicity. However, water solubility has been an enduring concern that needs to be addressed to facilitate pharmacological evaluations that tend to shy away from DMSO use. Applicant describes herein some ways to solve solubility hurdles in in vitro and in vivo settings, providing compounds that are more water-soluble yet preserve activity. In certain embodiments, water solubility of CMe in the presence of 5% methanol is between 0.2 to 0.3 mg/mL. In certain embodiments, provided compounds possess enhanced bioavailability and/or pharmacostability.

Applicant has unexpectedly found that compounds of the present invention are strong inhibitors of cancer cell migration. Such compounds display heightened activity in this regard compared to previously disclosed compounds. In certain embodiments, compounds of the present invention inhibit cancer cells from migrating from a primary tumor site to other locations throughout the body. In certain embodiments, compounds of the present invention inhibit the migratory processes that allow human metastatic breast cancer cells to egress from the circulation through the blood-brain barrier, and to subsequently migrate towards and along the abluminal surface of blood capillaries in the brain. In some embodiments, compounds of the present invention inhibit the migration of breast cancer cells. In some embodiments, compounds of the present invention inhibit the migration of lung cancer cells.

In some embodiments, the present invention provides compounds of formula I:

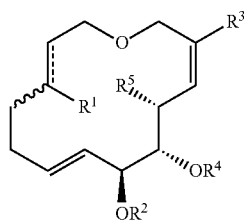

or a pharmaceutically acceptable salt thereof;
wherein:
≈ is a single or double bond;
$R^1$ is hydrogen or optionally substituted $C_{1-6}$ aliphatic;
$R^2$ is an oxygen protecting group, hydrogen, or optionally substituted $C_{1-6}$ aliphatic;
$R^3$ and $R^5$ are each independently optionally substituted $C_{1-6}$ aliphatic; and
$R^4$ is hydrogen or -T-Y;
-T- is an optionally substituted $C_{1-8}$ bivalent saturated or unsaturated, straight or branched, hydrocarbon chain, wherein one or more methylene units are optionally and independently replaced by —NR—, —N(R)C(O)—, —C(O)N(R)—, —N(R)SO$_2$—, —SO$_2$N(R)—, —O—, —C(O)—, —OC(O)—, —OC(O)O—, —C(O)O—, —OC(O)N(R)—, —S—, —SO—, or —SO$_2$—;
each R is independently —H, or an optionally substituted group selected from the group consisting of $C_{1-20}$ aliphatic, $C_{1-20}$ heteroaliphatic, 6- to 10-membered aryl, 5- to 12-membered heteroaryl, 3- to 14-membered carbocycle, 3- to 12-membered heterocyclic; and
—Y is hydrogen or acyl.

In some embodiments, $R^1$ is hydrogen. In some embodiments, $R^1$ is optionally substituted $C_{1-6}$ aliphatic. In some embodiments, $R^1$ is $C_{1-6}$ aliphatic substituted with one or more halogens. In some embodiments, $R^1$ is optionally substituted $C_{1-3}$ aliphatic. In some embodiments, $R^1$ is $C_{1-3}$ aliphatic substituted with one or more halogens. In some embodiments, $R^1$ is methyl. In other embodiments, $R^1$ is —CF$_3$.

In some embodiments, $R^2$ is an oxygen protecting group. In other embodiments, $R^2$ is hydrogen. In some embodiments, $R^2$ is optionally substituted $C_{1-6}$ aliphatic. In some embodiments, $R^2$ is optionally substituted $C_{1-3}$ aliphatic. In some embodiments, $R^2$ is methyl.

In certain embodiments, $R^3$ is optionally substituted $C_{1-6}$ aliphatic. In certain embodiments, $R^3$ is optionally substituted $C_{1-3}$ aliphatic. In some embodiments, $R^3$ is methyl.

In some embodiments, $R^4$ is hydrogen. In some embodiments, $R^4$ is other than hydrogen. In other embodiments, $R^4$ is -T-Y.

In some embodiments, $R^5$ is optionally substituted $C_{1-6}$ aliphatic. In some embodiments, $R^5$ is optionally substituted $C_{1-3}$ aliphatic. In some embodiments, $R^5$ is methyl.

In certain embodiments, -T- is an optionally substituted $C_{1-8}$ bivalent saturated or unsaturated, straight or branched, hydrocarbon chain, wherein one or more methylene units are optionally and independently replaced by —NR—, —N(R)C(O)—, —C(O)N(R)—, —O—, —C(O)—, —OC(O)—, —OC(O)O—, —C(O)O—, or —OC(O)N(R)—. In certain embodiments, -T- is an optionally substituted $C_{1-6}$ bivalent saturated or unsaturated, straight or branched, hydrocarbon chain, wherein one or more methylene units are optionally and independently replaced by —NR—, —N(R)C(O)—, —C(O)N(R)—, —O—, —C(O)—, —OC(O)—, —OC(O)O—, —C(O)O—, or —OC(O)N(R)—. In certain embodiments, -T- is an optionally substituted $C_{1-3}$ bivalent saturated or unsaturated, straight or branched, hydrocarbon chain, wherein one or two methylene units are optionally and independently replaced by —NR—, —N(R)C(O)—, —C(O)N(R)—, —O—, —C(O)—, —OC(O)—, —OC(O)O—, —C(O)O—, or —OC(O)N(R)—. In certain embodiments, -T- is —CH$_2$—.

In some embodiments, Y is hydrogen. In some embodiments, Y is other than hydrogen. In some embodiments, Y is acyl. In some embodiments, Y is —CO$_2$H. In some embodiments, Y is —CO$_2$R. In some embodiments, Y is —CO$_2$Me. In some embodiments, Y is —C(O)N(R)$_2$. In some embodiments, Y is —C(O)NHEt. In some embodiments, Y is —C(O)NHMe. In some embodiments, Y is —OH.

In some embodiments, $R^1$ is $C_{1-3}$ aliphatic substituted with one or more halogens, or $R^4$ is -T-Y wherein -T- is CH$_2$ and —Y is acyl. In some embodiments, $R^1$ is —CF$_3$, or $R^4$ is -T-Y wherein -T- is CH$_2$ and —Y is —CO$_2$H.

In some embodiments, -T- is —CH$_2$— and Y is selected from the group consisting of —CO$_2$R and —C(O)N(R)$_2$, wherein R is $C_{1-3}$ aliphatic. In some embodiments, -T- is —CH$_2$— and Y is selected from the group consisting of —CO$_2$R and —C(O)N(R)$_2$, wherein R is methyl or ethyl.

In some embodiments, -T- is —C(O)— and Y is —OR or N(R)$_2$. In some embodiments, -T- is —C(O)— and Y is —OR or N(R)$_2$, wherein R is hydrogen or $C_{1-3}$ aliphatic. In some embodiments, -T- is —C(O)— and Y is —OR or N(R)$_2$, wherein R is hydrogen, methyl, or ethyl. In some embodiments, T is a covalent bond and Y is selected from the group consisting of —CO$_2$R and —C(O)N(R)$_2$, wherein R is hydrogen or $C_{1-3}$ aliphatic. In some embodiments, T is —CH$_2$CH$_2$O— and Y is hydrogen.

In certain embodiments, $R^1$ is hydrogen or $C_{1-3}$ aliphatic substituted with one or more halogens, $R^2$ is $C_{1-3}$ aliphatic, $R^3$ is $C_{1-3}$ aliphatic, $R^4$ is hydrogen or -T-Y wherein -T- is a covalent bond or —CH$_2$— and Y is selected from the group consisting of —CO$_2$R and —C(O)N(R)$_2$, wherein R is hydrogen or $C_{1-3}$ aliphatic, $R^5$ is $C_{1-3}$ aliphatic, and ≈ is a single bond.

In certain embodiments, $R^1$ is hydrogen or $C_{1-3}$ aliphatic substituted with one or more halogens, $R^2$ is $C_{1-3}$ aliphatic, $R^3$ is $C_{1-3}$ aliphatic, $R^4$ is hydrogen or -T-Y wherein -T- is a covalent bond or —CH$_2$— and Y is selected from the group consisting of —CO$_2$R and —C(O)N(R)$_2$, wherein R is hydrogen or $C_{1-3}$ aliphatic, $R^5$ is $C_{1-3}$ aliphatic, and ≈ is a (Z)— double bond.

In certain embodiments, $R^1$ is hydrogen or $C_{1-3}$ aliphatic substituted with one or more halogens, $R^2$ is $C_{1-3}$ aliphatic, $R^3$ is $C_{1-3}$ aliphatic, $R^4$ is hydrogen or -T-Y wherein -T- is a covalent bond or —CH$_2$— and Y is selected from the group consisting of —CO$_2$R and —C(O)N(R)$_2$, wherein R is hydrogen or $C_{1-3}$ aliphatic, $R^5$ is $C_{1-3}$ aliphatic, and ≈ is an (E)- double bond.

In certain embodiments, $R^1$ is hydrogen, $R^2$ is methyl, $R^3$ is methyl, $R^4$ is -T-Y wherein -T- is —CH$_2$— and Y is selected from the group consisting of —CO₂R and —C(O)N(R)₂, wherein R is methyl, R⁵ is methyl, and ⁝⁝⁝ is a single bond.

In certain embodiments, R¹ is hydrogen, R² is methyl, R³ is methyl, R⁴ is -T-Y wherein -T- is —CH₂CH₂O— and Y is hydrogen, wherein R is methyl, R⁵ is methyl, and ⁝⁝⁝ is a single bond.

In certain embodiments, R¹ is hydrogen, R² is methyl, R³ is methyl, R⁴ is -T-Y wherein -T- is a covalent bond and Y—C(O)NHR, wherein R is ethyl, R⁵ is methyl, and ⁝⁝⁝ is a single bond.

In some embodiments, ⁝⁝⁝ is a double bond, R¹ is —CF₃, R², R³ and R⁵ are methyl, and R⁴ is hydrogen or -T-Y, wherein -T- is —CH₂— and Y is —CO₂H.

In some embodiments, ⁝⁝⁝ is a single or double bond, R¹ is hydrogen or methyl, R², R³ and R⁵ are methyl, and R⁴ is hydrogen or -T-Y, wherein -T- is —CH₂— and Y is —CO₂H. In some embodiments, ⁝⁝⁝ is a double bond, R¹ is hydrogen or methyl, R², R³ and R⁵ are methyl, and R⁴ is hydrogen or -T-Y, wherein -T- is —CH₂— and Y is —CO₂H. In some embodiments, where ⁝⁝⁝ is an (E)- double bond, R¹ is hydrogen or methyl, and R², R³ and R⁵ are methyl, R⁴ is hydrogen. In some embodiments, where ⁝⁝⁝ is a single bond, R¹ is hydrogen, and R², R³ and R⁵ are methyl, R⁴ is -T-Y, wherein -T- is —CH₂— and Y is —CO₂H.

In some embodiments, ⁝⁝⁝ is an (E)- double bond, R¹ is hydrogen or —CF₃, R², R³ and R⁵ are methyl, and R⁴ is hydrogen. In some embodiments, ⁝⁝⁝ is a (Z)— double bond, R¹ is methyl, R², R³ and R⁵ are methyl, and R⁴ is -T-Y, wherein -T- is —CH₂— and Y is —CO₂H.

In some embodiments, when ⁝⁝⁝ is a double bond, R¹ is hydrogen, R² is methyl, R³ is methyl, and R⁵ is methyl, R⁴ is not hydrogen.

In some embodiments, the present invention provides compounds of formula II, III, or IV:

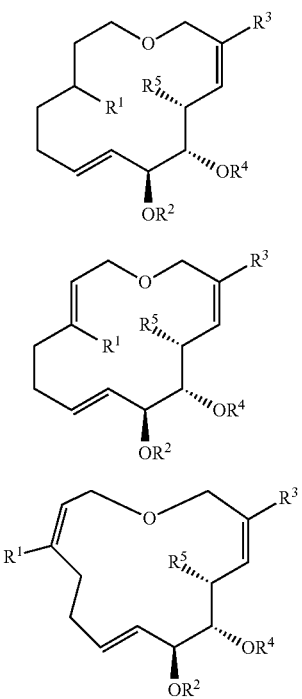

or a pharmaceutically acceptable salt thereof; wherein each of R¹, R², R³, R⁴, and R⁵ is as defined above and described in classes and subclasses herein, both singly and in combination.

In some embodiments, the present invention provides compounds of formula II-a, III-a, or IV-a:

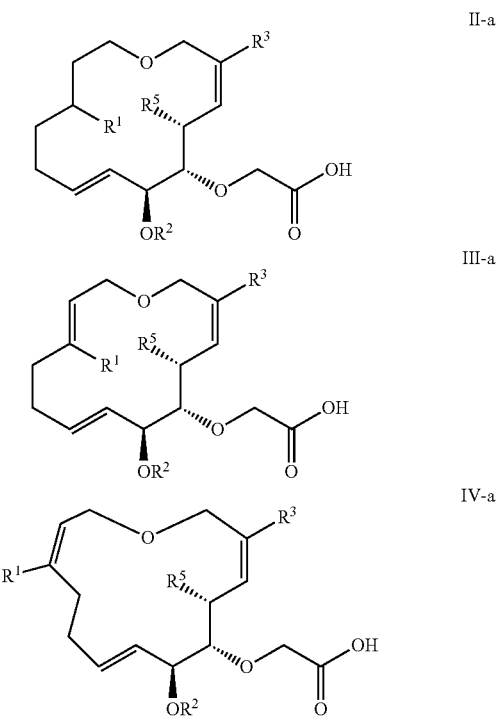

or a pharmaceutically acceptable salt thereof; wherein each of R¹, R², R³, and R⁵ is as defined above and described in classes and subclasses herein, both singly and in combination.

Exemplary compounds of formula I are depicted in Table A, below.

TABLE A

Carboxymethyl migraether
(CMME)

Carboxymethyl dehydromigraether
(CMDME)

TABLE A-continued
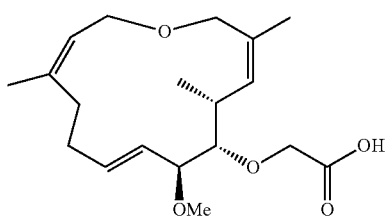 [SMILES: CO[C@H]1/C=C/CC/C(C)=C\COC/C(C)=C\[C@@H](C)[C@@H]1OCC(=O)O]
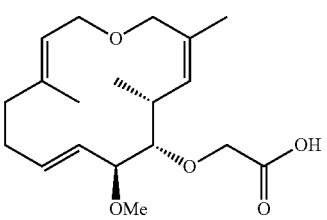 [SMILES: CO[C@H]1/C=C/CC/C(C)=C/COC/C(C)=C\[C@@H](C)[C@@H]1OCC(=O)O]
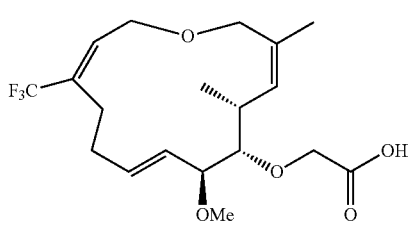 [SMILES: CO[C@H]1/C=C/CC/C(C(F)(F)F)=C\COC/C(C)=C\[C@@H](C)[C@@H]1OCC(=O)O]
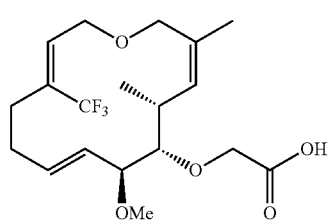 [SMILES: CO[C@H]1/C=C/CC/C(C(F)(F)F)=C/COC/C(C)=C\[C@@H](C)[C@@H]1OCC(=O)O]
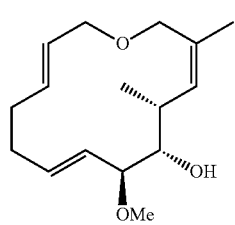 [SMILES: CO[C@H]1/C=C/CC/C=C/COC/C(C)=C\[C@@H](C)[C@@H]1O]
Dehydro migraether (DHME)
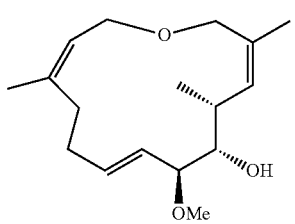
Methyl-cis-dehydromigraether
TABLE A-continued
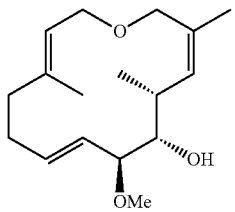 [SMILES: CO[C@H]1/C=C/CC/C(C)=C/COC/C(C)=C\[C@@H](C)[C@@H]1O]
Methyl-trans-dehydromigraether
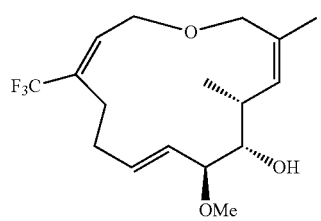 [SMILES: CO[C@H]1/C=C/CC/C(C(F)(F)F)=C\COC/C(C)=C\[C@@H](C)[C@@H]1O]
E-Trifluoromethyl dehydromigraether
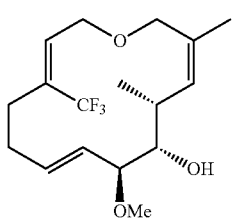 [SMILES: CO[C@H]1/C=C/CC/C(C(F)(F)F)=C/COC/C(C)=C\[C@@H](C)[C@@H]1O]
Z-Trifluoromethyl dehydromigraether
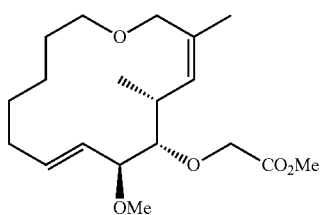 [SMILES: COC(=O)CO[C@H]1[C@H](C)/C=C(/C)COCCCCC/C=C/[C@@H]1OC]
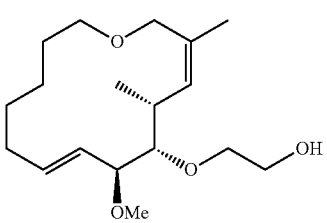 [SMILES: CO[C@H]1/C=C/CCCCCOC/C(C)=C\[C@@H](C)[C@@H]1OCCO]
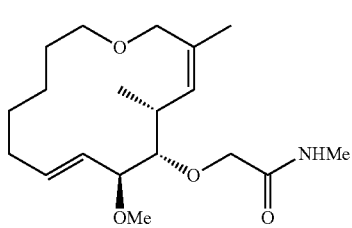 [SMILES: CNC(=O)CO[C@H]1[C@H](C)/C=C(/C)COCCCCC/C=C/[C@@H]1OC]

TABLE A-continued

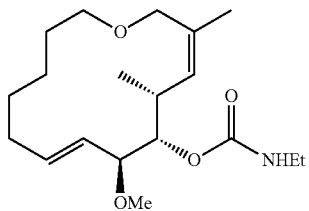

or a pharmaceutically acceptable salt thereof.

Throughout the disclosure, the compound in Table A labeled "carboxymethyl migraether" is referred to using a number of abbreviations. It will be appreciated that "cME", "CME", "CM-ME", "CMME", and "carboxymethyl-ME" all refer to this compound. In addition, "migrastatin ether" or "ME" refers to the compound of formula:

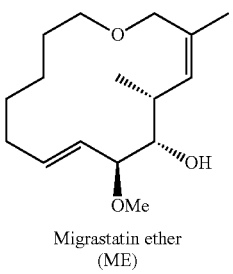

Migrastatin ether
(ME)

or a pharmaceutically acceptable salt thereof. In certain embodiments, the formulations and uses as described herein encompass ME. In certain embodiments, a compound of formula I is other than ME.

In some embodiments, compounds of the present invention include open-chain, acyclic versions of compounds of formula I.

Formulations

As described above, the present invention provides compounds and synthetic methodologies useful in the development of novel therapeutic agents, particularly for cancer therapeutics. In general, compound prepared as disclosed herein can be useful for the treatment and/or prevention, (preferably the prevention of metastasis), of cancer in a subject suffering therefrom.

Thus, the present invention provides pharmaceutical compositions for treating cancer and/or for preventing the recurrence of cancer, comprising any compound of the present invention disclosed herein, as an active ingredient, optionally in combination with a pharmaceutically acceptable carrier. Pharmaceutical compositions of the present invention may further comprise other therapeutically active ingredients (e.g., chemotherapeutic and/or palliative). For example, palliative treatment encompasses painkillers, antinausea medications and anti-sickness drugs. In addition, chemotherapy, radiotherapy, and surgery can all be used palliatively (that is, to reduce symptoms without going for cure; e.g., for shrinking tumors and reducing pressure, metastasis, bleeding, pain and other symptoms of cancer).

In certain embodiments, pharmaceutical compositions or methods of the invention comprise an immunological adjuvant, or a combination of immunological adjuvants.

Compounds of the present invention may be combined with a pharmaceutically acceptable carrier to form a pharmaceutical composition. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. In certain embodiments, a pharmaceutical composition includes a pharmaceutically acceptable amount of an inventive compound. In certain embodiments, a pharmaceutical composition includes a therapeutically effective amount of an inventive compound. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

Wetting agents, emulsifiers, and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof, and coloring agents. In the case of capsules, tablets and pills, the pharmaceutical compositions may also comprise buffering agents. Solid compositions of a similar type may also be employed as fillers in soft and hard-shelled gelatin capsules using such carriers as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

Drug-eluting forms include coated or medicated stents and implantable devices. Drug-eluting stents and other devices may be coated with a compound or pharmaceutical preparation and may further comprise a polymer designed for time-release.

In certain embodiments, a compound or pharmaceutical preparation is administered orally. In other embodiments, the compound or pharmaceutical preparation is administered intravenously. In certain embodiments, a compound is attached via a cleavable linker to a solid support that is administered with a catheter. Alternative routes of administration include sublingual, intramuscular, and transdermal administrations.

When the compounds of the present invention are administered as pharmaceuticals, to humans and animals, they can be given per se or as a pharmaceutical composition containing, for example, 0.1% to 99.5%, or 0.5% to 90%, of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

These compounds may be administered to humans and other animals for therapy by any suitable route of administration, including orally, nasally, as by, for example, an aerosol, a spray, rectally, intravaginally, parenterally, intracisternally and topically, as by powders, ointments or drops, including buccally and sublingually.

Regardless of the route of administration selected, compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In some embodiments, a chronic treatment involves administering a compound or pharmaceutical composition of the invention repeatedly over the life of the subject. Preferred chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above.

Generally doses of the compounds of this invention for a patient, when used for the indicated effects, will range from about 0.0001 to about 100 mg per kg of body weight per day. In some embodiments, the daily dosage will range from 0.001 to 50 mg of compound per kg of body weight. In some embodiments, the daily dosage will range from 0.01 to 10 mg of compound per kg of body weight. In some embodiments, the daily dosage will range from 0.01 to 1 mg of compound per kg of body weight. In some embodiments, a compound is administered in the range of approximately 0.01 mg/kg body weight to 200 mg/kg body weight. In some embodiments, a compound is administered in the range of approximately 0.1 mg/kg body weight to 200 mg/kg body weight. In some embodiments, a compound is administered in the range of approximately 1 mg/kg body weight to 200 mg/kg body weight. In some embodiments, a compound is administered in the range of approximately 10 mg/kg body weight to 200 mg/kg body weight. In some embodiments, a compound is administered in the range of approximately 10 mg/kg body weight to 40 mg/kg body weight. In some embodiments, a compound is administered in the range of approximately 40 mg/kg body weight to 200 mg/kg body weight. In some embodiments, a compound is administered in the range of approximately 10 mg/kg body weight to 20 mg/kg body weight. In some embodiments, a compound is administered in the range of approximately 10 mg/kg body weight to 40 mg/kg body weight. However, lower or higher doses can be used. In some embodiments, the dose administered to a subject may be modified as the physiology of the subject changes due to age, disease progression, weight, or other factors. Such doses may correspond to doses found useful and appropriate in an applicable animal model (e.g., in a transgenic rodent model). In some embodiments, such dosages useful in an experimental model range from about 10 mg/kg body weight to about 200 mg/kg. In certain embodiments, the dosage in an experimental animal ranges from about 10 mg/kg body weight to about 40 mg/kg body weight. In certain embodiments, the dosage in an experimental animal ranges from about 40 mg/kg body weight to about 200 mg/kg body weight. In certain embodiments, the dosage used in an applicable animal model is approximately 10 mg/kg, approximately 12 mg/kg, approximately 20 mg/kg, approximately 40 mg/kg, approximately 49 mg/kg, approximately 100 mg/kg, or approximately 200 mg/kg.

If desired, the effective daily dose of the active compound may be administered as two, three, four, five, six, or more sub-doses administered separately at appropriate intervals throughout the day, optionally, in unit dosage forms.

While it is possible for a compound of the present invention to be administered alone, it is preferable to administer the compound as a pharmaceutical formulation (composition) as described above.

The compounds according to the invention may be formulated for administration in any convenient way for use in human or veterinary medicine, by analogy with other pharmaceuticals.

The invention provides kits comprising pharmaceutical compositions of an inventive compound. In certain embodiments, such kits include the combination of a compound of the present invention and another chemotherapeutic agent. The agents may be packaged separately or together. The kit optionally includes instructions for prescribing the medication. In certain embodiments, the kit includes multiple doses of each agent. The kit may include sufficient quantities of each component to treat a subject for a week, two weeks, three weeks, four weeks, or multiple months. The kit may include a full cycle of chemotherapy. In certain embodiments, the kit includes multiple cycles of chemotherapy.

In certain embodiments, compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. In certain embodiments, an anticancer agent is an epothilone, taxol, radicicol or TMC-95A/B. In certain embodiments, the epothilone is 12,13-desoxyepothilone B, (E)-9,10-dehydro-12,13-desoxyEpoB and 26-CF3-(E)-9,10-dehydro-12,13-desoxyEpoB. Additionally, the present invention also encompasses the use of certain cytotoxic or anticancer agents currently in clinical trials and which may ultimately be approved by the FDA (including, but not limited to, epothilones and analogues thereof and geldanamycins and analogues thereof).

EXAMPLES

Experimental Details

Analytical Equipment:

Optical rotations were measured on a JASCO P-2000 digital polarimeter at rt. Concentration (c) in g/100 ml and solvent are given in parentheses. $^1$H— and $^{13}$C-NMR spectra were recorded on a Bruker AMX-400 or a Bruker DRX-500 spectrometer in CDCl$_3$. Chemical shifts (δ-values) are reported in ppm with residual undeuterated CDCl$_3$ as the internal standard (referenced to 7.26 ppm for $^1$H-NMR and 77.0 ppm for $^{13}$C-NMR). Coupling constants (J) (H,H) are given in Hz, spectral splitting patterns are designated as singlet (s), doublet (d), triplet (t), quadruplet (q), multiplet or more overlapping signals (m), apparent (app), broad signal (br). Low resolution mass spectra (ionspray, a variation of electrospray) were acquired on a Perkin-Elmer Sciex API 100 spectrometer. Samples were introduced by direct infusion. High resolution mass spectra (fast atom bombardment, FAB) were acquired on a spectrometer. Flash chromatography (FC) was performed with E. Merck silica gel (60, particle size 0.040-0.063 mm).

Techniques, Solvents, and Reagents:

Reactions involving air or moisture-sensitive reagents or intermediates were performed under argon or nitrogen atmosphere in glassware which had been heat gun or flame-dried under high vacuum. Indicated reaction temperatures refer to those of the reaction bath, while room temperature (rt) is noted as 22° C. Preparative reactions were stirred magnetically. Tetrahydrofuran (THF), methylene chloride (CH$_2$Cl$_2$), and toluene were obtained from a dry solvent system (activated alumina columns, positive pressure of argon). All other solvents were used as received in Sure/Seal bottles (Aldrich). All other reagents were purchased from Aldrich at the highest commercial quality and used without further purification.

Example 1

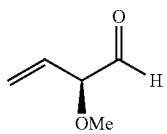

4

To the hot soluble solution of NaIO$_4$ (14.95 g, 69.9 mmol) in H$_2$O (32 mL) at 70° C., was added silica gel (40 g, 40-60 μm). The suspension was cooled to rt and added CH$_2$Cl$_2$ (300 mL) and sonicated for 10 min. The diol 3 (10.15 g, 50 mmol) in CH$_2$Cl$_2$ (50 mL) was added. After the suspension was stirred at rt for 45 min, the mixture was filtered and washed with dry CH$_2$Cl$_2$ (100 mL). The solution was again dried over anhydrous Na$_2$SO$_4$ and filtered and washed with dry CH$_2$Cl$_2$ (50 mL) to get the desired aldehyde 4 in CH$_2$Cl$_2$ (500 mL). The aldehyde solution can be used directly to the next step to make dihydropyrone.

Example 2

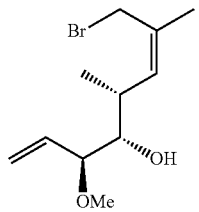

12

(3S,4S,5R,Z)-8-Bromo-3-methoxy-5,7-dimethyl-octa-1,6-dien-4-ol (12)

Method 1: The allylic alcohol 11 (6.2 g, 30.97 mmol) and 2,6-lutidine (4.3 mL, 37.08 mmol) were combined in anhydrous CH$_3$CN (350 mL). Carbon tetrabromide (16.2 g, 49.44 mmol) was added and the solution was chilled to 0° C. Ph$_3$P (10.53 g, 40.17 mmol) was added in portions and the mixture was allowed to warm to rt. After stirring for 30 min, the reaction was quenched by pouring into sat. NH$_4$Cl (200 mL). The aqueous phase was extracted with Et$_2$O (2×200 mL) and the combined organic extracts were dried (MgSO$_4$), filtered and concentrated. The residue was filtered through a plug of silica gel (EtOAc-hexanes, 1:19) and concentrated. The resulting residue was purified by flash chromatography (EtOAc-hexanes, 1:9) to afford allylic bromide 12 (6.9 g, 85%) as a colorless oil. $[\alpha]^{20}$D−7.01 (c 1.0, CHCl$_3$); $^1$H NMR (CDCl$_3$, 400 MHz): δ 5.75 (m, 1H), 5.36-5.27 (m, 3H), 4.04 (d, 1H, J=9.6 Hz), 3.96 (d, 1H, J=9.7 Hz), 3.48 (dd, 1H, J=5.1, 8.0 Hz), 3.29 (m+s, 4H), 2.67 (m, 1H), 2.59 (d, 1H, J=5.2 Hz), 1.85 (s, 3H), 1.04 (d, 3H, J=6.8 Hz); $^{13}$C NMR (100 MHz, CDCl$_3$): δ 135.7, 134.7, 131.5, 119.9, 83.9, 77.3, 56.7, 35.6, 32.6, 22.4, 15.8; HRMS (ESI) calcd for [C$_{11}$H$_{19}$O$_2$Br+Na]$^+$: 285.0466. found: 285.0475.

Method 2: To a solution of allylic alcohol 11 (3.9 g, 19.5 mmol) in CH$_2$Cl$_2$ (100 ml) at rt was added solid supported PPh$_3$ (3 mmol/g, 9.5 g) and CBr$_4$ (8.4 g, 25.4 mmol). After stirring for 20 min, the reaction mixture was filtered through a cotton plug and concentrated. The resulting residue was purified by flash chromatography to get 4.24 g allylic bromide 12 (83%).

Example 3

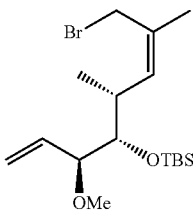

13

((3 S,4S,5R,Z)-8-Bromo-3-methoxy-5,7-dimethylocta-1, 6-dien-4-yloxy)(tert-butyl)dimethylsilane (13): To a solution of secondary alcohol 12 (5.04 g, 19.23 mmol) in CH$_2$Cl$_2$ (150 mL) at −15° C. was added 2,6-lutidine (3.4 mL, 28.85 mmol) and TBSOTf (6.2 mL, 26.92 mmol). After stirring at −15° C. for 1 h, the reaction mixture was quenched with MeOH (20 mL) at −15° C. The mixture was treated with saturated NH$_4$Cl aqueous solution. The organic layer was separated and the aqueous layer was extracted with CH$_2$Cl$_2$ (3×). The combined organic layers were washed with brine, dried (MgSO$_4$), filtered and concentrated. Purification of the crude product by flash chromatography (EtOAc-hexanes, 1:9) to afford bromide 13 (6.6 g, 91%) as a yellow oil. $[\alpha]^{20}$D 2.76 (c 1.5, CHCl$_3$); $^1$H NMR (CDCl$_3$, 400 MHz): δ 5.61 (m, 1H), 5.35 (d, 1H, J=9.8 Hz), 5.23 (m, 2H), 3.88 (s, 2H), 3.48 (dd, 1H, J=3.0, 7.1 Hz), 3.30 (t, 1H, J=7.5 Hz), 3.15 (s, 3H), 2.53 (m, 1H), 1.75 (s, 3H), 0.88 (m+s, 12H), 0.05 (s, 3H), 0.02 (s, 3H); $^{13}$C NMR (100 MHz, CDCl$_3$): δ 136.8, 135.6, 130.1, 119.2, 86.5, 78.0, 56.6, 35.1, 32.8, 26.5, 22.3, 18.9, 13.9, −3.4, −4.4; HRMS (ESI) calcd for [C$_{17}$H$_{33}$BrO$_2$Si+Na]$^+$: 399.1331. found: 399.1321.

Ether (15)

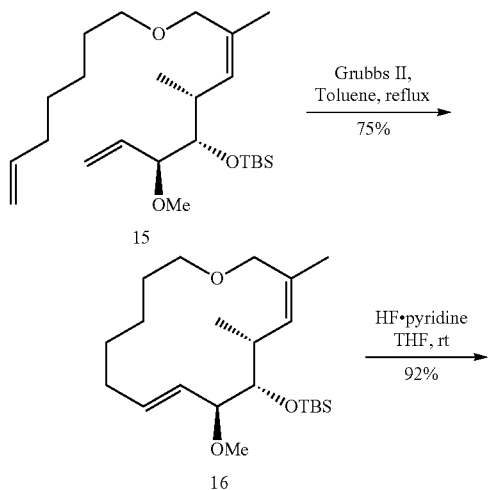

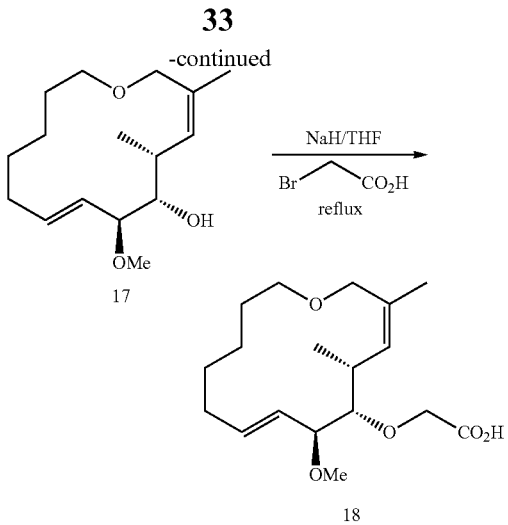

Example 4

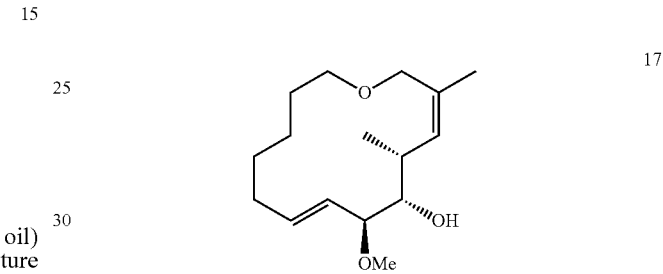

NaH (1.44 g, 36.16 mmol, 60% suspension in mineral oil) was suspended in anhydrous THF (120 mL), and the mixture was cooled to 0° C. 6-hepten-ol 14 (3.95 mL, 28.93 mmol) in THF (20 mL) was added, and the solution was stirred at 0° C. for 10 min. The ice bath was removed and stirring was continued at rt for 1 hr before cooling to 0° C. The solution of allylic bromide 13 (6.8 g, 18.08 mmol) in THF (30 mL) was added dropwise, followed by TBAI (67 mg, 0.18 mmol) and after 15 min, the ice bath was removed. Stirring was continued at rt overnight. The reaction was quenched with saturated aqueous NH$_4$Cl. The organic layer was separated and the aqueous was extracted with Et$_2$O (3×). The combined organic layers the combined organic extracts were dried (MgSO$_4$), filtered and concentrated. The resulting residue was purified by flash chromatography (CH$_2$Cl$_2$-hexanes, 3:1 to 1:1) to afford ether 15 (6.79 g, 90%) as a colorless oil. [α]$^{20}$D+1.55 (c 1.2, CHCl$_3$); $^1$H NMR (CDCl$_3$, 500 MHz): δ 5.80 (m, 1H), 5.62 (m, 1H), 5.38-5.23 (m, 3H), 5.01-4.92 (m, 2H), 3.95 (d, 1H, J=11.5 Hz), 3.85 (d, 1H, J=11.5 Hz), 3.44 (dd, 1H, J=3.0, 7.1 Hz), 3.38-3.30 (m, 3H), 3.20 (s, 3H), 2.62 (m, 1H), 2.04 (m, 2H), 1.72 (s, 3H), 1.60-1.55 (m, 2H), 1.41-1.33 (m, 4H), 0.91 (s+m, 12H), 0.05 (s, 3H), 0.02 (s, 3H); $^{13}$C NMR (CDCl$_3$, 125 MHz): δ 139.2, 135.6, 134.1, 130.9, 118.7, 114.5, 86.4, 78.8, 69.9, 69.4, 56.3, 34.1, 33.9, 29.8, 29.0, 26.4, 26.0, 21.7, 18.8, 14.5, −3.6, −4.6; HRMS (ESI) calcd for [C$_{24}$H$_{46}$O$_3$Si+Na]$^+$: 433.3114. found: 433.3098.

Example 5

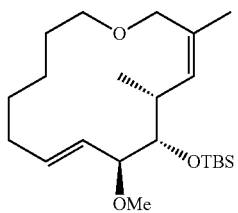

To the refluxing toluene (1 L) was added solutions of ether 15 (210 mg, 0.51 mmol) in toluene (10 mL) and Grubbs-II catalyst (87 mg, 20 mol %) in toluene (10 mL). After stirring for 15 min, DMSO (0.3 ml) was added and the reaction was cooled to rt and concentrated. Purification of the crude product by flash chromatography (EtOAc-hexanes, 1:20) to afford macroether 16 (140 mg, 75%) as a colorless oil. [α]$^{20}$D+49.45 (c 1.7, CHCl$_3$); $^1$H NMR (CDCl$_3$, 500 MHz): δ 5.59 (m, 1H), 5.51 (d, 1H, J=9.8 Hz), 5.24 (dd, 1H, J=8.4, 15.5 Hz), 3.87 (d, 1H, J=9.8 Hz), 3.65 (d, 1H, J=9.8 Hz), 3.53-3.49 (m, 2H), 3.43 (d, 1H, J=8.7 Hz), 3.36 (m, 1H), 3.20 (s, 3H), 2.91 (m, 1H), 2.18-2.14 (m, 2H), 1.74 (s, 3H), 1.68 (m, 1H), 1.55 (s, 3H), 1.50-1.36 (m, 5H), 0.91 (s, 9H), 0.88 (d, 3H, J=6.7 Hz), 0.05 (s, 3H), 0.03 (s, 3H); $^{13}$C NMR (CDCl$_3$, 125 MHz): δ 135.4, 134.2, 129.8, 129.7, 85.6, 78.7, 69.9, 69.2, 56.2, 34.0, 30.4, 27.0, 26.4, 23.4, 23.3, 18.9, 13.0, −3.5, −4.8; HRMS (ESI) calcd for [C$_{22}$H$_{42}$O$_3$Si+Na]$^+$: 405.2801. found: 405.2800.

Example 6

To a solution of TBS-macroether 16 (845 mg, 2.21 mmol) in THF (80 mL) at rt was added HF.pyridine (18 mL). After stirring for 24 h, the reaction mixture was carefully treated with saturated NaHCO$_3$ (450 mL) and diluted with Et$_2$O. The organic layer was separated and the aqueous layer was extracted with Et$_2$O (3×). The combined organic extracts were dried (MgSO$_4$), filtered and concentrated. The resulting residue was purified by flash chromatography (hexanes/EtOAc 10:1 to 4:1) to afford macroether 17 (544 mg, 92%) as a white amorphous solid. [α]$^{23}$D+104.42 (c 1.0, CHCl$_3$); $^1$H NMR (CDCl$_3$, 500 MHz): δ 5.67-5.60 (m, 2H), 5.22 (dd, 1H, J=7.6, 15.5 Hz), 3.76 (s, 2H), 3.56-3.52 (m, 1H), 3.49-3.40 (m, 3H), 3.30 (s, 3H), 2.93 (m, 1H), 2.73 (br s, 1H), 2.24 (m, 1H), 2.09 (m, 1H), 1.76 (d, 1H, J=1.2 Hz), 1.66 (m, 1H), 1.54-1.47 (m, 1H), 1.45-1.36 (m, 4H), 0.94 (d, 3H, J=6.9 Hz); $^{13}$C NMR (CDCl$_3$, 125 MHz): δ 135.9, 134.0, 130.2, 129.1, 84.5, 76.7, 69.7, 69.1, 56.2, 32.1, 30.5, 27.0, 26.8, 23.1, 12.7; HRMS (ESI) calcd for [C$_{16}$H$_{28}$O$_3$+Na]$^+$: 291.1936. found: 291.1937.

Sodium hydride (60 mg, 1.5 mmol, 60% in mineral oil) was washed with n-hexane (4×1 mL) and dried in vacuo. The resultant residue was suspended in THF (2.0 mL). Alcohol 17 (80 mg, 0.3 mmol) dissolved in THF (4.0 mL) was added to the NaH suspension and stirred for 1 hr at rt. A solution of bromoacetic acid (80 mg, 0.6 mmol) in THF (2.0 mL) was added. The reaction was refluxed at 85° C. for 14 hr and subsequently cooled to room temperature. The reaction was quenched dropwise with 2 M HCl and then acidified to pH 1. The aqueous layer was extracted with ethyl acetate (4×20 mL). The combined organic layers were dried over Na$_2$SO$_4$. Concentration of the solvent in vacuo afforded the acid which was purified by flash chromatography (hexanes/EtOAc 10:3 to 10:4) to afford acid 18 (CME) (67 mg, 70%) as a colorless film and 25 mg of starting material alcohol 17 (ME) was recovered. [α]²⁰D+184.44 (c, 1.4, CHCl₃); ¹H NMR (CDCl₃, 500 MHz): δ 12.09 (brs, 1H), 5.73 (m, 1H), 5.34 (d, 1H, J=10.1 Hz), 5.24 (dd, 1H, J=8.5, 15.5 Hz), 4.43 (d, 1H, J⁻17.3 Hz), 4.03 (d, 1H, J⁻17.3 Hz), 3.91 (d, 1H, J=10.7 Hz), 3.71 (t, 1H, J=9.0 Hz), 3.64 (d, 1H, J=10.7 Hz), 3.49 (m, 2H), 3.39 (s, 3H), 3.24 (d, 1H, J=9.4 Hz), 3.16 (m, 1H), 2.22 (m, 2H), 1.75 (s, 3H), 1.68 (m, 1H), 1.43 (m, 2H), 1.40-1.32 (m, 3H), 0.93 (d, 3H, J=6.7 Hz); ¹³C NMR (CDCl₃, 125 MHz): δ 172.7, 137.3, 132.1, 132.0, 127.3, 89.5, 83.5, 71.7, 70.2, 70.0, 56.0, 33.2, 30.2, 26.6, 26.5, 23.3, 23.2, 12.9; HRMS (ESI) calcd for [C₁₈H₃₀O₅+Na]⁺: 349.1991. found: 349.1992.

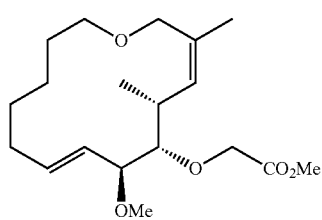

42

Ester 42.

A mixture of acid 18 (10.5 mg) in anhydrous MeOH (0.30 mL) and anhydrous PhMe (0.30 mL) was cooled to 0° C., treated with TMSCHN₂ (0.080 mL, 2.0 M in Et₂O) and stirred at this temperature for 1 h, 45 min. The volatiles were removed in vacuo and the product was purified by chrom. on SiO₂ (Hexanes:EtOAc, 4:1) to afford 42 (9.8 mg, 90%) as a clear oil: [α]_D²⁴+45.0 (c 1, CHCl₃); ¹H NMR (C₆D₆, 500 MHz) δ 6.05 (d, J=9.9 Hz, 1H), 5.41 (td, J=15.6, 6.6 Hz, 1H), 5.19 (dd, J=15.6, 8.2 Hz, 1H), 4.57, 4.41 (AB, J=16.2 Hz, 2H), 3.77 (t, J=8.3 Hz, 1H), 3.69, 3.66 (AB, J=10.9 Hz, 2H), 3.37-3.35 (m, 4H), 3.32-3.28 (m, 1H), 3.25-3.22 (m, 2H), 3.12 (s, 3H), 2.00-1.96 (m, 2H), 1.77 (d, J=0.9 Hz, 3H), 1.46-1.26 (m, 4H), 1.23 (d, J=6.9 Hz, 3H), 1.17-1.12 (m, 2H); ¹³C NMR (C₆D₆, 125 MHz) δ 171.0, 133.9, 133.7, 129.9, 129.6, 87.2, 86.5, 71.0, 70.7, 69.7, 55.8, 50.7, 33.6, 30.4, 27.6, 27.1, 23.5, 23.1, 14.0; MS-ESI calc for C₁₉H₃₂O₅Na (M+Na) 363.2. found 363.1.

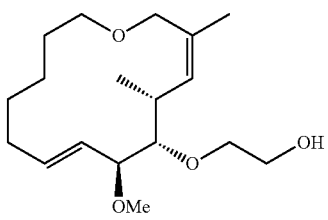

43

Compound 43. A mixture of ester 42 (13.0 mg, 0.0383 mmol) in anhydrous PhMe (1.0 mL) was cooled to −78° C., a solution of DIBAL (0.096 mL, 0.096 mmol, c=1.0 in hexanes) was added and the reaction mixture was allowed to warm up to 0° C. and stirred for 2 h. An additional portion of DIBAL (0.040 mL) was introduced, the mixture was stirred for 3 h, quenched with Rochelle's salt, extracted (3×EtOAc) and the combined organic layers were washed with water, brine, dried (MgSO₄), and concentrated. Purification by chrom. on SiO₂ (Hexanes:EtOAc, 3:1) afforded 43 (0.0071 g, 59%) as a clear oil: [α]D₂₄+59.7 (c 1.0 CHCl₃); ¹H NMR (C₆D₆, 600 MHz) δ 5.71 (d, J=10.2 Hz, 1H), 5.46 (td, J=15.5, 7.1 Hz, 1H), 5.25 (dd, J=15.5, 8.3 Hz, 1H), 4.07 (br s, 1H), 3.97-3.94 (m, 2H), 3.81 (d, J=4.0 Hz, 2H), 3.79-3.76 (m, 1H), 3.73 (t, J=8.7 Hz, 1H), 3.66 (d, J=10.8 Hz, 1H), 3.48 (dd, J=9.1, 1.4 Hz, 1H), 3.40-3.38 (m, 2H), 3.32-3.27 (m, 1H), 3.23 (s, 3H), 2.08-2.05 (m, 2H), 1.85 (d, J=1.2 Hz, 3H), 1.60-1.51 (m, 2H), 1.41-1.39 (m, 4H), 1.23 (d, J=6.8 Hz, 3H), 1.23-1.22 (m, 1H); ¹³C NMR (C₆D₆, 150 MHz) δ 134.5, 133.5, 130.6, 129.6, 87.4, 85.4, 76.5, 70.4, 69.8, 63.1, 56.0, 34.1, 30.3, 27.2, 27.0, 23.5, 23.3, 13.6; MS-ESI calc for C₁₈H₃₂O₄Na (M+Na) 335.2. found 335.3.

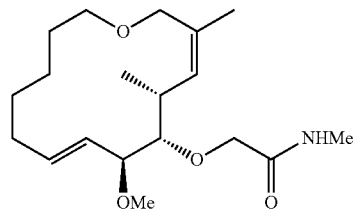

44

Compound 44.

A mixture of acid 18 (7.8 mg, 0.0239 mmol), MeNH₂—HCl (3.2 mg, 0.0378 mmol) and Hünig's base (0.00416 mL, 0.239 mmol) in anhydrous CH₂Cl₂ (0.50 mL) was treated with WSC.HCl (9.2 mg, 0.0478 mmol) and stirred under N₂ for 24 h. The reaction mixture was poured into water, extracted with EtOAc (3×5 mL) and the combined organic layers were washed with water, brine, dried (MgSO₄), and concentrated. Purification by chrom. on SiO₂ (Hexanes:EtOAc, 1:3) afforded 44 (7.2 mg, 89%) as a clear oil: [α]_D+41 (c 1.0, CHCl₃); ¹H NMR (C₆D₆, 600 MHz) δ Major rotamer: 7.45 (br s, 1H), 5.41 (d, J=10.1 Hz, 1H), 5.34 (td, J=15.6, 7.1 Hz, 1H), 5.09 (dd, J=15.5, 8.5 Hz, 1H), 4.38, 4.33 (AB, J=15.7 Hz, 2H), 3.66 (dd, J=10.9, 0.7 Hz, 1H), 3.53 (t, J=8.8 Hz, 1H), 3.40 (d, J=10.8 Hz, 1H), 3.27-3.13 (m, 4H), 3.03 (s, 3H), 1.99-1.96 (m, 2H), 1.63 (d, J=1.4 Hz, 3H), 1.48-1.21 (m, 8H), 1.08-1.04 (m, 1H), 1.02 (d, J=6.8 Hz, 3H); Minor rotamer (representative signals), 5.89 (dd, J=10.8, 1.5 Hz, 1H), 5.25-5.20 (m, 1H), 4.91 (dd, J=15.5, 8.9 Hz, 1H), 3.44 (t, J=8.7 Hz, 1H), 2.98 (s, 3H), 1.92 (d, J=1.4, 3 H), 0.94 (d, J=6.8 Hz, 3H); ¹³C NMR (C₆D₆, 150 MHz) δ 170.7, 135.0, 132.8, 131.3, 129.1, 87.8, 85.0, 73.7, 70.3, 69.8, 55.8, 33.6, 30.2, 27.0, 26.8, 25.3, 23.4, 23.1, 13.5; ESI-MS calc for C₁₉H₃₃NO₄Na, 362.2. found 362.2.

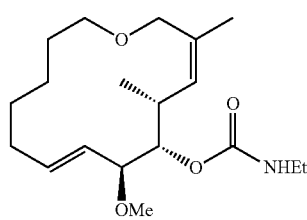

45

Compound 45. A mixture of compound 17 (ME) (10.7 mg, 0.0399 mmol), EtNCO (9.5 μL, 0.120 mmol), and Et₃N (16.8 μL, 0.120 mmol) in anhydrous PhMe (1.0 mL) was heated under reflux for 24 h, cooled to rt and the volatiles were removed in vacuo. Purification by chrom. on SiO₂ (Hexanes:EtOAc, 2:1) afforded 45 (0.0071 g, 53%) as a light-yellow oil: [α]D₂₄+34.1 (c 1, CHCl₃); ¹H NMR (C₆D₆, 600 MHz) δ Major rotamer: 5.63 (d, J=9.9 Hz, 1H), 5.50-5.45 (m, 1H), 5.31 (dd, J=15.7, 8.6 Hz, 1H), 4.24 (s, 1H), 4.11 (app. t, J=5.5 Hz, 1H), 3.69-3.8 (m, 1H), 3.60-3.59 (m, 1H), 3.45-3.39 (m, 1H), 3.31-3.23 (m, 2H), 3.21 (s, 3H), 3.18 (s, 1H), 2.98 (app. t, J=6.2 Hz, 2H), 2.03-1.92 (m, 3H), 1.67 (d, J=1.3 Hz, 3H), 1.52-1.40 (m, 2H), 1.38-1.30 (m, 4H), 1.19 (d, J=6.6. Hz, 3H), 1.12-1.08 (m, 2H); Minor rotamer (representative signals) 6.17 (dd, J=10.6, 1.4 Hz, 1H), 5.05 (dd, J=15.6, 8.7 Hz, 1H); $^{13}$C NMR ($C_6D_6$, 150 MHz) δ Major rotamer: 156.6, 135.2 (2), 131.9, 130.9, 84.0, 77.9, 71.0, 69.7, 56.1, 53.3, 34.6, 32.7, 30.1, 26.9, 26.6, 23.5, 23.1, 14.6; Minor rotamer (representative signals) 64.3, 36.0, 30.4, 21.44; MS-ESI calc for $C_{19}H_{33}NO_4Na$ (M+Na) 362.2. found 362.3.

Example 7

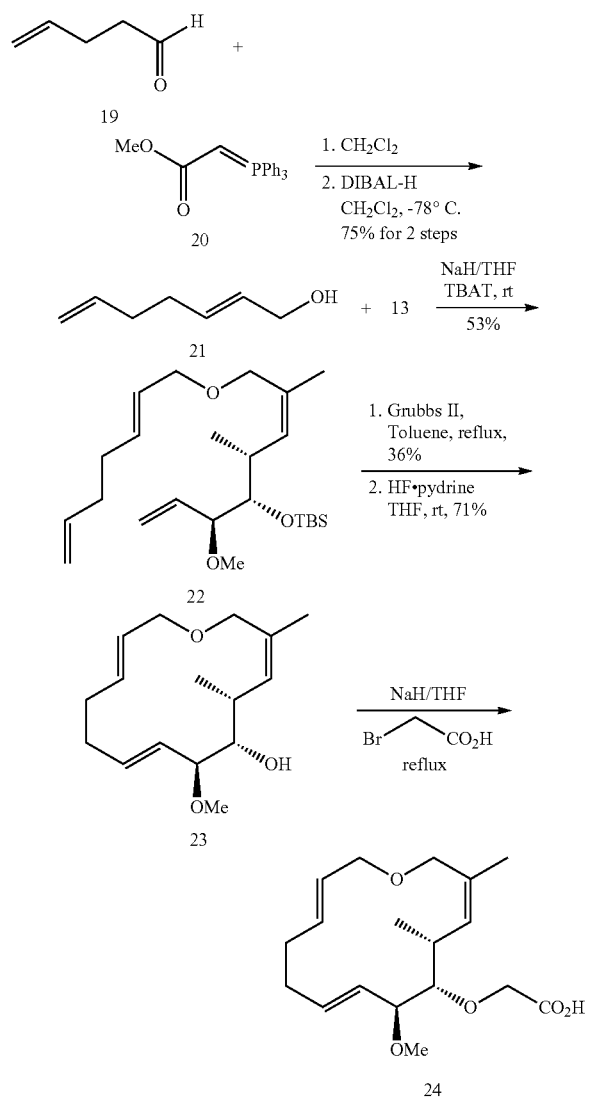

TBS-ether 22: NaH (32 mg, 0.8 mmol, 60% suspension in mineral oil) was suspended in anhydrous THF (3 mL), and the mixture was cooled to 0° C. (E)-hepta-2,6-dien-1-ol 21 (72 mg, 0.64 mmol) in THF (2 mL) was added, and the solution was stirred at 0° C. for 10 min. The ice bath was removed and stirring was continued at rt for 1 hr before cooling to 0° C. The solution of allylic bromide 13 (150 mg, 0.4 mmol) in THF (3 mL) was added dropwise, followed by TBAI (2 mg) and after 15 min, the ice bath was removed. Stirring was continued at rt overnight. The reaction was quenched with saturated aqueous NH$_4$Cl. The organic layer was separated and the aqueous was extracted with Et$_2$O (3×). The combined organic layers the combined organic extracts were dried (MgSO$_4$), filtered and concentrated. The resulting residue was purified by flash chromatography (CH$_2$Cl$_2$-hexanes, 3:1 to 1:1) to afford ether 22 (90 mg, 53%) as a colorless oil. $^1$H NMR (CDCl$_3$, 500 MHz): δ 5.80 (m, 1H), 5.67-5.58 (m, 3H), 5.37 (d, J=9.5 Hz, 1H), 5.28 (m, 3H), 4.98 (m, 2H), 3.95 (d, J=11.3 Hz, 1H), 3.83 (m, 2H), 3.40 (m, 2H), 3.19 (s+m, 4H), 2.58 (m, 1H), 2.13 (complex, 4H), 1.72 (s, 3H), 0.90 (s+d, 12H), 0.05, (s, 3H), 0.02 (s, 3); $^{13}$C NMR (CDCl$_3$, 125 MHz): δ 138.3, 135.5, 134.4, 137.7, 130.7, 127.2, 118.8, 115.0, 86.5, 78.8, 70.5, 68.6, 56.33, 34.2, 33.5, 31.9, 26.4, 21.7, 18.8, 14.3, −3.6, −4.6; HRMS (ESI) calcd for $[C_{24}H_{44}O_3Si+Na]^+$: 431.2957. found: 431.2957.

TBS-Macroether:

To the refluxing toluene (450 mL) was added solutions of ether 22 (90 mg, 0.22 mmol) in toluene (10 mL) and Grubbs-II catalyst (38 mg, 20 mol %) in toluene (10 mL). After stirring for 15 min, DMSO (0.1 ml) was added and the reaction was cooled to rt and concentrated. Purification of the crude product by flash chromatography (EtOAc-hexanes, 1:20) to afford macroether (30 mg, 35%) as a colorless oil. MS (ESI) calcd for $[C_{22}H_{40}O_3Si+Na]^+$: 403.26. found: 403.2.

Macroether 23

To a solution of TBS-macroether (44 mg, 0.16 mmol) in THF (5 mL) at rt was added HF.pyridine (1.5 mL). After stirring for 24 h, the reaction mixture was carefully treated with saturated NaHCO$_3$ (50 mL) and diluted with Et$_2$O. The organic layer was separated and the aqueous layer was extracted with Et$_2$O (3×). The combined organic extracts were dried (MgSO$_4$), filtered and concentrated. The resulting residue was purified by flash chromatography (hexanes/EtOAc 10:1 to 4:1) to afford macroether 23 (22 mg, 71%). $[α]^{20}$D+346.31 (c 0.5, CHCl$_3$); $^1$H NMR (CDCl$_3$, 500 MHz): δ 5.63 (m, 1H), 5.53) m, 2H), 5.42 (m, 1H), 5.18 (dd, J=8.5, 15.6 Hz, 1H), 3.95 (m, 2H), 3.80 (dd, J=6.7, 14.3 Hz, 1H), 3.63 (d, J=10.2 Hz, 1H), 3.41 (t, J=9.1 Hz, 1H), 3.29 (s+m, 4H), 2.75 (br, 1H), 2.68 (m, 1H), 2.42-2.34 (m, 2H), 2.21-2.14 (m, 2H), 1.78 (s, 3H), 0.93 (d, J=6.8 Hz, 3H); $^{13}$C NMR (CDCl$_3$, 125 MHz): δ 136.1, 135.1, 134.3, 131.1, 129.3, 127.8, 84.3, 77.8, 69.3, 65.9, 56.5, 32.0, 31.9, 30.7, 22.3, 12.8; HRMS (ESI) calcd for $[C_{16}H_{26}O_3+Na]^+$: 289.1780. found: 289.1769.

Acid 24 (8 mg, 55%), $[α]^{20}{}_D$+108.79 (c 0.35, 1:4 MeOH/CHCl$_3$); $^1$H NMR (CDCl$_3$, 500 MHz): δ $^{13}$C NMR (CDCl$_3$, 125 MHz): δ HRMS (ESI) calcd for $[C_{18}H_{28}O_5+Na]^+$: 347.1834. found: 347.1826.

Example 8

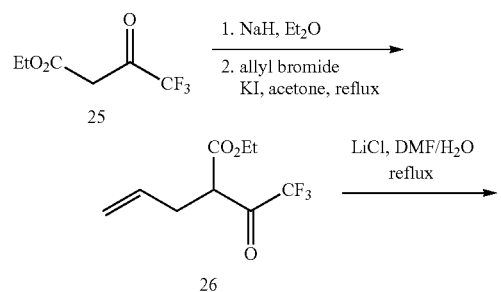

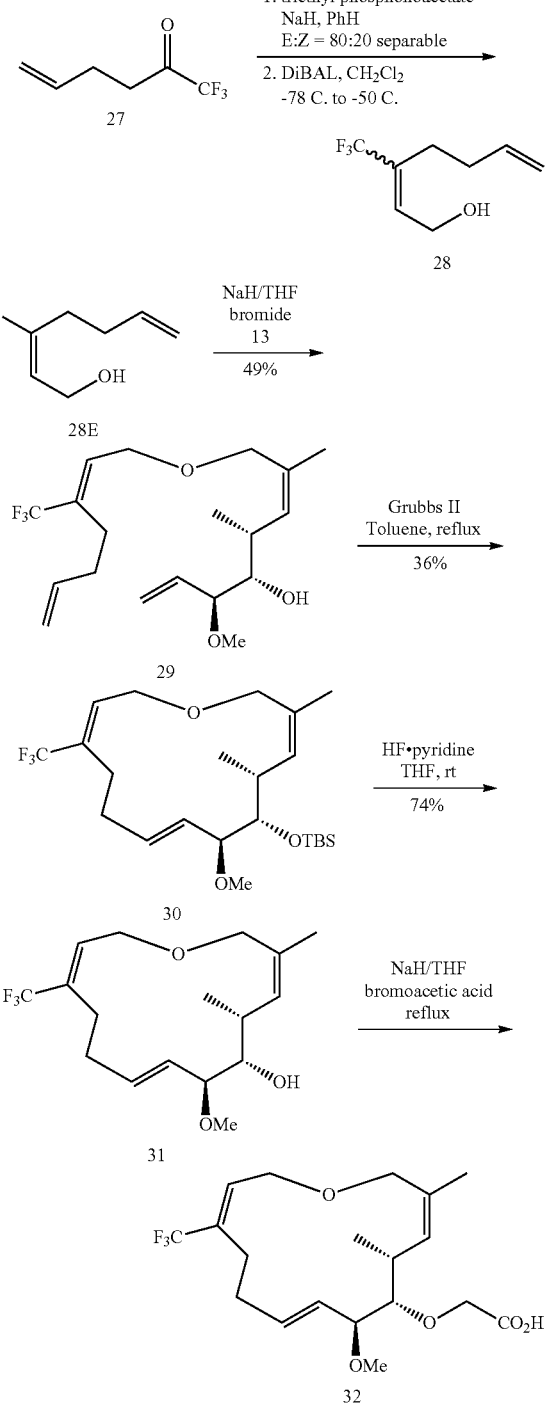

overnight. The reaction was quenched with saturated aqueous NH$_4$Cl. The organic layer was separated and the aqueous was extracted with Et$_2$O (3×). The combined organic layers the combined organic extracts were dried (MgSO$_4$), filtered and concentrated. The resulting residue was purified by flash chromatography (CH$_2$Cl$_2$-hexanes, 3:1 to 1:1) to afford ether 29 (136 mg, 49%) as a colorless oil. [α]$^{20}$D−4.19 (c 1.0, CHCl$_3$); $^1$H NMR (CDCl$_3$, 500 MHz): δ 6.26 (t, J=5.8 Hz, 1H), 5.77 (m, 1H), 5.60 (m, 1H), 5.42 (d, J=9.6 Hz, 1H), 5.27 (m, 2H), 5.02 (m, 1H), 4.01 (m, 2H), 3.99 (d, J=11.3 Hz, 1H), 3.89 (d, J=11.3 Hz, 1H), 3.40 (m, 2H), 3.2 (s+m, 4H), 2.58 (m, 1H), 2.29-2.19 (m, 4H), 1.73 (s, 3H), 0.90 (s+d, 12H), 0.06, 0.02; $^{13}$C NMR (CDCl$_3$, 125 MHz): δ 137.1, 135.5, 135.1, 132.1 (q, $^3J_{C-F}$=6.1 Hz), 130.8 (q, $^2J_{C-F}$=28.6 Hz), 129.9, 125.3 (q, $^1J_{C-F}$=273.5 Hz), 118.8, 115.9, 86.3, 78.8, 69.5, 65.3, 56.3, 34.3, 33.0, 26.2, 25.9, 21.7, 18.8, 14.4, −3.59, −4.6; $^{19}$F NMR (CDCl$_3$, MHz): δ −67.4. HRMS (ESI) calcd for [C$_{25}$H$_{43}$F$_3$O$_3$Si+Na]$^+$: 499.2831. found: 499.2838.

TBS-Macroether 30:

To the refluxing toluene (570 mL) was added solutions of ether 29 (136 mg, 0.28 mmol) in toluene (10 mL) and Grubbs-II catalyst (50 mg, 20 mol %) in toluene (10 mL). After stirring for 15 min, DMSO (0.1 ml) was added and the reaction was cooled to rt and concentrated. Purification of the crude product by flash chromatography (EtOAc-hexanes, 1:20) to afford macroether (46 mg, 36%) as a colorless oil. [α]$^{20}$D−2.20 (c 0.9, CHCl$_3$); $^1$H NMR (CDCl$_3$, 500 MHz): δ 6.31 (bt, 1H), 5.67 (m, 1H), 5.51-5.45 (m, 2H), 4.02 (m, 3H), 3.75 (d, J=11.8 Hz, 1H), 3.50 (m, 2H), 3.26 (s, 3H), 2.52 (m, 1H), 2.38-2.32 (m, 4H), 1.71 (s, 3H), 0.09 (s, 9H), 0.88 (d, J=6.9 Hz, 3H), 0.07 (s, 3H), 0.06 (s, 3H); $^{13}$C NMR (CDCl$_3$, 125 MHz): δ 135.2, 133.4 (q, $^3J_{C-F}$=5.9 Hz), 131.0, 130.5 (q, $^2J_{C-F}$=27.8 Hz), 129.6, 128.9, 124.3 (q, $^1J_{C-F}$=272.6 Hz), 84.4, 77.6, 68.8, 64.8, 57.1, 34.9, 30.1, 26.3, 26.0, 22.1, 18.6, 17.1, −3.79, −4.59; $^{19}$F NMR (CDCl$_3$, MHz): δ −65.9; MS (ESI) calcd for [C$_{23}$H$_{39}$F$_3$O$_3$Si+Na]$^+$: 471.25. found: 471.1.

Macroether 31

To a solution of TBS-macroether (48 mg, 0.11 mmol) in THF (5 mL) at rt was added HF.pyridine (1.5 mL). After stirring for 24 h, the reaction mixture was carefully treated with saturated NaHCO$_3$ (50 mL) and diluted with Et$_2$O. The organic layer was separated and the aqueous layer was extracted with Et$_2$O (3×). The combined organic extracts were dried (MgSO$_4$), filtered and concentrated. The resulting residue was purified by flash chromatography (hexanes/EtOAc 10:1 to 4:1) to afford macroether 23 (27 mg, 74%). [α]$^{20}$D 142.6 (c 1.1, CHCl$_3$); $^1$H NMR (CDCl$_3$, 500 MHz): δ 6.31 (btr, J=5.5 Hz, 1H), 5.74 (m, 1H), 5.61 (d, J=9.4 Hz, 1H), 5.39 (dd, J=6.9, 15.7 Hz, 1H), 4.03-3.96 (m, 3H), 3.73 (d, J=11.8 Hz, 1H), 3.39 (m, 2H), 3.26 (s, 3H), 2.87 (br, 1H), 2.53 (m, 1H), 2.41-2.30 (m, 4H), 1.74 (s, 3H) m 0.93 (d, J=6.9 Hz, 3H); $^{13}$C NMR (CDCl$_3$, 125 MHz): δ 134.7, 134.2, 133.2 (q, $^3J_{C-F}$=5.9 Hz), 130.7 (q, $^2J_{C-F}$=30.1 Hz), 130.2, 130.1, 125.2 (q, $^1J_{C-F}$=270.1 Hz), 82.9, 76.4, 69.2, 65.1, 56.5, 33.1, 29.5, 26.4, 22.5, 15.6; $^{19}$F NMR (CDCl$_3$, MHz): δ −65.78. HRMS (ESI) calcd for [C$_{17}$H$_{25}$O$_3$F$_3$+Na]$^+$: 357.1653. found: 357.1650.

Acid 32 (14 mg, 45%), [α]$^{20}$D 75.38 (c 0.6, CHCl$_3$); $^1$H NMR (CDCl$_3$, 500 MHz): δ 11.98 (br, OH), $^{13}$C NMR (CDCl$_3$, 125 MHz): δ $^{19}$F NMR (CDCl$_3$, MHz): δ HRMS (ESI) calcd for [C$_{19}$H$_{27}$O$_5$F$_3$+Na]$^+$: 415.1708. found: 415.1691.

E and Z 3-(trifluoromethyl)hepta-2,6-dien-1-ol 28 were synthesized by the reference 1 and 2. TBS-ether 29: NaH (47 mg, 1.2 mmol, 60% suspension in mineral oil) was suspended in anhydrous THF (3 mL), and the mixture was cooled to 0° C. Alcohol 28E (180 mg, 0.94 mmol) in THF (2 mL) was added, and the solution was stirred at 0° C. for 10 min. The ice bath was removed and stirring was continued at rt for 1 hr before cooling to 0° C. The solution of allylic bromide 13 (210 mg, 0.56 mmol) in THF (3 mL) was added dropwise, followed by TBAI (2 mg) and after 15 min, the ice bath was removed. Stirring was continued at rt

Example 9

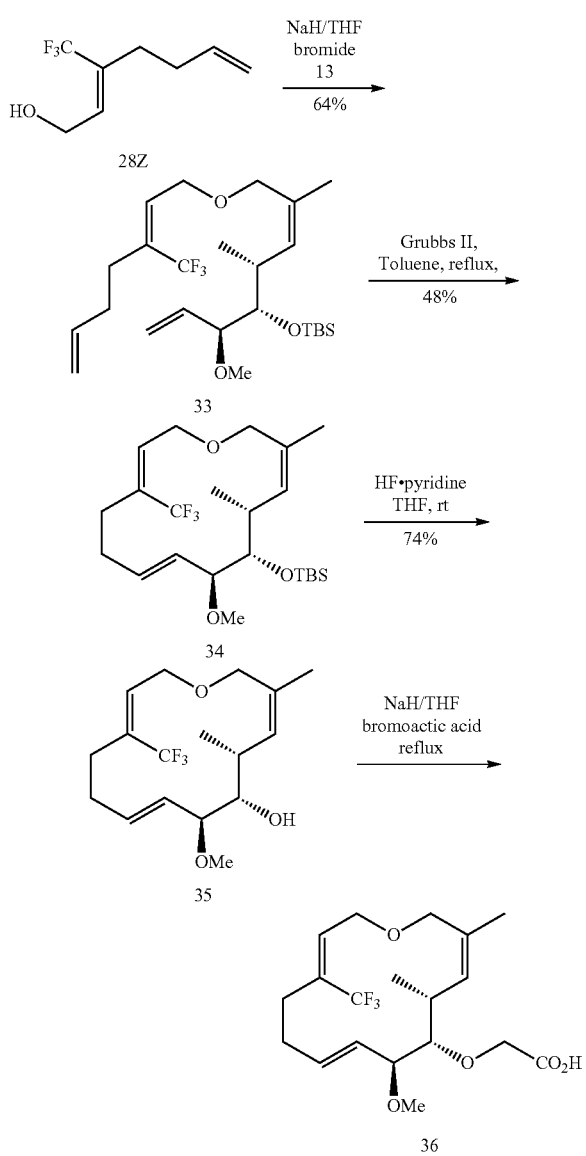

TBS-ether 33:NaH (50 mg, 1.3 mmol, 60% suspension in mineral oil) was suspended in anhydrous THF (3 mL), and the mixture was cooled to 0° C. Alcohol 28Z (150 mg, 0.83 mmol) in THF (2 mL) was added, and the solution was stirred at 0° C. for 10 min. The ice bath was removed and stirring was continued at rt for 1 hr before cooling to 0° C. The solution of allylic bromide 13 (210 mg, 0.56 mmol) in THF (3 mL) was added dropwise, followed by TBAI (2 mg) and after 15 min, the ice bath was removed. Stirring was continued at rt overnight. The reaction was quenched with saturated aqueous NH$_4$Cl. The organic layer was separated and the aqueous was extracted with Et$_2$O (3×). The combined organic layers the combined organic extracts were dried (MgSO$_4$), filtered and concentrated. The resulting residue was purified by flash chromatography (CH$_2$Cl$_2$-hexanes, 3:1 to 1:1) to afford ether 33 (170 mg, 64%) as a colorless oil. $[\alpha]^{20}$D 1.83 (c 1.0, CHCl$_3$); $^1$H NMR (CDCl$_3$, 500 MHz): δ 5.83-5.75 (m, 2H), 5.60 (m, 1H), 5.26 (m, 2H), 5.02 (m, 2H), 4.13 (brs, 2H), 3.96 (d, J=11.0 Hz, 1H), 3.88 (d, J=11.2 Hz, 1H), 3.43 (m, 1H), 3.38 (m, 1H), 3.20 (s, 3H), 2.59 (m, 1H), 2.25 (m, 4H), 1.73 (s, 3H), 0.89 (s+d, 12H), 0.05 (s, 3H), 0.02 (s, 3H); $^{13}$C NMR (CDCl$_3$, 125 MHz): δ 137.0, 135.5, 135.4 (q, $^3J_{C-F}$=3.1 Hz), 135.0, 130.0, 129.6 (q, $^2J_{C-F}$=26.3 Hz), 129.9, 124.3 (q, $^1J_{C-F}$=272.5 Hz), 118.8, 115.9, 86.3, 78.7, 68.8, 65.8, 56.7, 34.4, 31.1, 28.7, 26.4, 22.6, 18.7, 15.4, −3.7, −4.7; $^{19}$F NMR (CDCl$_3$, MHz): δ −61.2; HRMS (ESI) calcd for [C$_{25}$H$_{43}$F$_3$O$_3$Si+Na]$^+$: 499.2831. found: 499.2832.

TBS-Macroether 34:

To the refluxing toluene (700 mL) was added solutions of ether 33 (166 mg, 0.35 mmol) in toluene (10 mL) and Grubbs-II catalyst (60 mg, 20 mol %) in toluene (10 mL). After stirring for 15 min, DMSO (0.1 ml) was added and the reaction was cooled to rt and concentrated. Purification of the crude product by flash chromatography (EtOAc-hexanes, 1:20) to afford macroether (67 mg, 48%) as a colorless oil. $[\alpha]^{20}$D 122.52 (c 1.0, CHCl$_3$); $^1$H NMR (CDCl$_3$, 500 MHz): δ 5.73 (m, 1H), 5.58 (m, 1H), 5.45 (d, J=9.2 Hz, 1H), 5.26 (m, 1H), 4.19 (m, 2H), 3.90 (d, J=10.1 Hz, 1H), 3.65 (d, J=10.1 Hz, 1H), 3.45 (s, 2H), 3.20 (s, 3H), 2.59 (m, 1H), 2.49-2.31 (m, 4H), 1.75 (s, 3H), 0.89 (s+d, 12H), 0.03 (s, 3H), 0.01 (s, 3H); $^{13}$C NMR (CDCl$_3$, 125 MHz): δ 137.0, 136.2 (q, $^3J_{C-F}$=3.0 Hz), 132.2, 130.8, 130.4 (q, $^2J_{C-F}$=28.6 Hz), 129.8, 124.3 (q, $^1J_{C-F}$=274.6 Hz), 85.3, 79.6, 67.7, 64.9, 56.5, 33.9, 29.7, 29.4, 26.3, 22.4, 18.8, 12.9, −3.7, −4.9; $^{19}$F NMR (CDCl$_3$, MHz): δ −60.2; MS (ESI) calcd for [C$_{23}$H$_{39}$F$_3$O$_3$Si+Na]$^+$: 471.25. found: 471.3.

Macroether 35

To a solution of TBS-macroether (74 mg, 0.16 mmol) in THF (5 mL) at rt was added HF.pyridine 2.5 mL). After stirring for 24 h, the reaction mixture was carefully treated with saturated NaHCO$_3$ (50 mL) and diluted with Et$_2$O. The organic layer was separated and the aqueous layer was extracted with Et$_2$O (3×). The combined organic extracts were dried (MgSO$_4$), filtered and concentrated. The resulting residue was purified by flash chromatography (hexanes/EtOAc 10:1 to 4:1) to afford macroether 35 (27 mg, 74%). $[\alpha]^{20}$D 254.34 (c 0.75, CHCl$_3$); $^1$H NMR (CDCl$_3$, 500 MHz): δ 5.72 (btr, J=5.7 Hz, 1H), 5.64-5.58 (m, 2H), 5.21 (dd, J=8.1, 15.5 Hz, 1H), 4.13 (m, 2H), 3.85 (d, J=10.2 Hz, 1H), 3.74 (d, J=10.1 Hz, 1H), 3.41 (m, 1H), 3.47 (m, 1H), 3.27 (s, 3H), 2.75 (s, 1H), 2.56 (m, 2H), 2.52-2.23 (m, 3H), 1.78 (s, 3H), 0.95 (d, J=6.7 Hz, 3H); $^{13}$C NMR (CDCl$_3$, 125 MHz): δ 136.24 (q, $^3J_{C-F}$=3.0 Hz), 135.50, 134.42, 130.43, 130.42, 130.3 (q, $^2J_{C-F}$=22.8 Hz), 124.17 (q, $^1J_{C-F}$=274.8 Hz), 84.14, 77.28, 67.60, 64.80, 56.61, 32.20, 30.24, 29.83, 22.39, 12.81; $^{19}$F NMR (CDCl$_3$, MHz): δ −59.9; HRMS (ESI) calcd for [C$_{17}$H$_{25}$O$_3$F$_3$+Na]$^+$: 357.1653. found: 357.1658.

Acid 36 (10 mg, 25%), $[\alpha]^{20}$D 99.67 (c 0.4, CHCl$_3$); $^1$H NMR (CDCl$_3$, 500 MHz): δ $^{13}$C NMR (CDCl$_3$, 125 MHz): δ $^{19}$F NMR (CDCl$_3$, MHz): δ HRMS (ESI) calcd for [C$_{19}$H$_{27}$O$_5$F$_3$+Na]$^+$: 415.1708. found: 415.1691.

Example 10

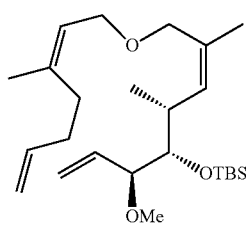

TBS-ether 37: NaH (46 mg, 1.2 mmol, 60% suspension in mineral oil) was suspended in anhydrous THF (3 mL), and the mixture was cooled to 0° C. cis-2,3-Dimethyl-2,6-octadien-1-ol (154 mg, 0.73 mmol) in THF (2 mL) was added, and the solution was stirred at 0° C. for 10 min. The ice bath was removed and stirring was continued at rt for 1 hr before cooling to 0° C. The solution of allylic bromide 13 (170 mg, 0.45 mmol) in THF (3 mL) was added dropwise, followed by TBAI (2 mg) and after 15 min, the ice bath was removed. Stirring was continued at rt overnight. The reaction was quenched with saturated aqueous NH$_4$Cl. The organic layer was separated and the aqueous was extracted with Et$_2$O (3×). The combined organic layers the combined organic extracts were dried (MgSO$_4$), filtered and concentrated. The resulting residue was purified by flash chromatography (CH$_2$Cl$_2$-hexanes, 3:1 to 1:1) to afford ether 37 (150 mg, 74%) as a colorless oil. [α]$^{20}$D−1.78 (c 1.0, CHCl$_3$); $^1$H NMR (CDCl$_3$, 500 MHz): δ 5.61 (m, 1H), 5.38-5.23 (m, 4H), 5.09 (m, 1H), 3.96 (d, J=11.3 Hz, 1H), 3.87-3.81 (m, 3H), 3.44-3.35 (m, 2H), 3.20 (s, 3H), 2.61 (m, 1H), 2.06 (m, 4H), 1.74 (s, 3H), 1.73 (s, 3H), 1.68 (s, 3H), 1.60 (s, 3H), 0.90 (s+d, 12H), 0.05, 0.02; $^{13}$C NMR (CDCl$_3$, 125 MHz): δ 140.4, 135.6, 134.3, 132.1, 130.9, 124.1, 123.3, 118.7, 86.4, 78.8, 68.8, 66.2, 56.3, 34.2, 32.5, 26.9, 26.4, 25.9, 23.7, 21.7, 18.8, 17.9, 14.3, −3.6, −4.6.

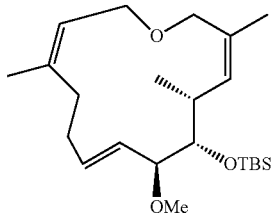

38

TBS-Macroether 38:

To the refluxing toluene (660 mL) was added solutions of ether 37 (150 mg, 0.32 mmol) in toluene (10 mL) and Grubbs-II catalyst (70 mg, 20 mol %) in toluene (10 mL). After stirring for 15 min, DMSO (0.1 ml) was added and the reaction was cooled to rt and concentrated. Purification of the crude product by flash chromatography (EtOAc-hexanes, 1:20) to afford macroether (36 mg, 28%) as a colorless oil. $^1$H NMR (CDCl$_3$, 500 MHz): δ 5.70 (m, 1H), 5.69-5.52 (m, 2H), 5.37 (d, J=9.2 Hz, 1H), 3.95-3.90 (m, 3H), 3.72 (d, J=11.0 Hz, 1H), 3.44 (m, 1H), 3.38 (t, J=6.7 Hz, 1H), 3.19 (s, 3H), 2.64 (m, 1H), 2.32-2.26 (m, 3H), 2.19 (m, 1H), 1.75 (s, 3H), 1.72 (s, 3H), 0.90 (s, 9H), 0.87 (d, J=6.8 Hz, 3H), 0.05 (s, 3H), 0.02 (s, 3H); $^{13}$C NMR (CDCl$_3$, 125 MHz): δ 139.7, 134.7, 132.6, 130.4, 129.1, 123.6, 84.4, 78.6, 68.8, 65.8, 56.7, 34.4, 31.1, 28.7, 26.3, 22.6, 22.5, 18.7, 15.4, −3.7, −4.7; MS (ESI) calcd for [C$_{23}$H$_{42}$O$_3$Si+Na]$^+$: 417.28. found: 417.2.

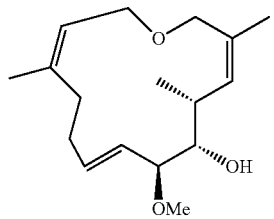

39

Macroether 39

To a solution of TBS-macroether (36 mg, 0.09 mmol) in THF (5 mL) at rt was added HF.pyridine (1.5 mL). After stirring for 24 h, the reaction mixture was carefully treated with saturated NaHCO$_3$ (50 mL) and diluted with Et$_2$O. The organic layer was separated and the aqueous layer was extracted with Et$_2$O (3×). The combined organic extracts were dried (MgSO$_4$), filtered and concentrated. The resulting residue was purified by flash chromatography (hexanes/EtOAc 10:1 to 4:1) to afford macroether 39 (17 mg, 67%). [α]$^{20}$D (c, CHCl$_3$); $^1$H NMR (CDCl$_3$, 500 MHz): δ 5.73 (m, 1H), 5.76 (d, J=9.3 Hz, 1H), 5.46 (t, J=6.7 Hz, 1H), 5.38 (dd, J=6.7, 15.8 Hz, 1H), 3.99 (d, J=11.1 Hz, 1H), 3.86 (m, 2H), 3.67 (d, J=11.1 Hz, 1H), 3.40 (m, 2H), 3.29 (s, 3H), 2.80 (br, 1H), 2.66 (m, 1H), 2.31-2.19 (m, 4H), 1.76 (s, 3H), 1.75 (s, 3H), 0.91 (d, J=13.6 Hz, 3H); $^{13}$C NMR (CDCl$_3$, 125 MHz): δ 139.3, 135.0, 134.2, 130.9, 129.1, 123.7, 83.1, 76.7, 69.1, 66.0, 56.4, 32.6, 31.7, 28.6, 22.8, 22.6, 14.0; HRMS (ESI) calcd for [C$_{17}$H$_{28}$O$_3$+Na]$^+$: 303.1936. found: 303.1940.

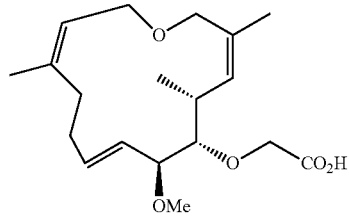

39a

Compound 39a is made following the procedure in example 9 preparing compound 36. $^1$H NMR (CDCl$_3$, 500 MHz): δ HRMS (ESI) 5.83 (m, 1H), 5.52-5.43 (m, 2H), 5.29 (d, J=10.0 Hz, 1H), 4.37 (d, J=17.3 Hz, 1H), 4.02 (d, J=17.3 Hz, 1H), 3.95 (d, J=11.0 Hz, 1H), 3.87 (t, J=10.7 Hz, 1H), 3.79 (dd, J=7.4, 7.7 Hz, 1H), 3.64 (m, 2H), 3.37 (s, 3H), 3.28 (d, J=9.2 Hz, 1H), 2.80 (m, 1H), 2.39-2.17 (m, 4H), 1.75 (s, 3H), 1.65 (s, 3H), 0.89 (d, J=9.5 Hz, 3H); calcd for [C$_{19}$H$_{30}$O$_5$+Na]$^+$: 361.1991. found: 361.2002.

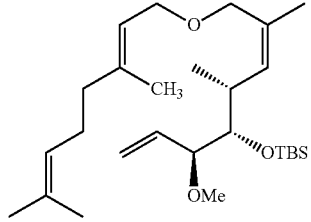

40

Example 11

TBS-ether 40: NaH (42 mg, 1.0 mmol, 60% suspension in mineral oil) was suspended in anhydrous THF (3 mL), and the mixture was cooled to 0° C. Geraniol (131 mg, 0.85 mmol) in THF (2 mL) was added, and the solution was stirred at 0° C. for 10 min. The ice bath was removed and stirring was continued at rt for 1 hr before cooling to 0° C. The solution of allylic bromide 13 (200 mg, 0.53 mmol) in THF (3 mL) was added dropwise, followed by TBAI (2 mg) and after 15 min, the ice bath was removed. Stirring was continued at rt overnight. The reaction was quenched with saturated aqueous NH$_4$Cl. The organic layer was separated and the aqueous was extracted with Et$_2$O (3×). The combined organic layers the combined organic extracts were dried (MgSO$_4$), filtered and concentrated. The resulting residue was purified by flash chromatography (CH$_2$Cl$_2$-hexanes, 3:1 to 1:1) to afford ether 40 (138 mg, 58%) as a colorless oil. [α]$^{20}$D 3.54 (c 1.0, CHCl$_3$); $^1$H NMR (CDCl$_3$, 500 MHz): δ 5.61 (m, 1H), 5.39-5.23 (m, 4H), 5.09 (m, 1H), 3.97 (d, J=11.3 Hz, 1H), 3.89-3.82 (m, 3H), 3.45-3.35 (m, 2H), 3.20 (s, 3H), 2.61 (m, 1H), 2.10 (m, 2H), 2.02 (m, 2H), 1.74 (s, 3H), 1.68 (s, 3H), 1.65 (s, 3H), 1.60 (s, 3H), 0.90 (s+d, 12H), 0.05, 0.02; $^{13}C$ NMR (CDCl$_3$, 125 MHz): δ 140.4, 135.6, 134.3, 131.9, 130.9, 124.3, 121.2, 118.8, 86.4, 78.8, 68.8, 66.4, 56.3, 39.8, 34.2, 26.6, 26.4, 25.9, 21.7, 18.8, 17.9, 16.7, 14.3, −3.6, −4.6.

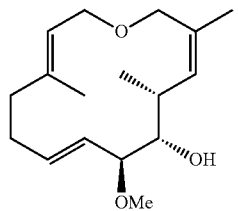

41

Compound 41 is made following the procedure in example 10 preparing compound 39, wherein the ring closing metathesis product was further desilylated in a manner similar to that of compound 38. $[α]^{20}D$ 161.9 (c 1.9, CHCl$_3$); $^1H$ NMR (CDCl$_3$, 500 MHz): δ 5.64 (m, 1H), 5.54 (d, J=9.5 Hz, 1H), 5.26 (t, J=6.8 Hz, 1H), 5.16 (dd, J=8.2, 8.3 Hz, 1H), 3.99 (m, 2H), 3.86 (d, J=9.5 Hz, 1H), 3.62 (d, J=9.5 Hz, 1H), 3.39 (t, J=8.9 Hz, 1H), 3.29 (s+m, 4H), 2.74 (s, 1H), 2.63 (m, 1H), 2.34-2.28 (m, 3H), 2.15 (m, 1H), 1.76 (s, 3H), 1.66 (s, 3H), 0.92 (d, J=6.8 Hz, 3H); $^{13}C$ NMR (CDCl$_3$, 125 MHz): δ 139.3, 135.9, 134.9, 131.2, 128.8, 122.6, 84.3, 77.4, 66.3, 65.2, 56.5, 37.8, 31.9, 29.4, 22.6, 16.5, 12.8; HRMS (ESI) calcd for $[C_{17}H_{28}O_3+Na]^+$: 303.1936. found: 303.1935.

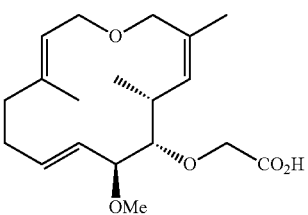

41a

Compound 41a is made following the procedure in example 9 preparing compound 36. $[α]^{20}{}_D$ 138.16 (c 0.8, CHCl$_3$); $^1H$ NMR (CDCl$_3$, 500 MHz): δ 5.75 (m, 1H), 5.32 (d, J=9.6 Hz, 1H), 5.22 (t, J=7.2 Hz, 1H), 5.18 (dd, J=8.5, 8.1 Hz, 1H), 4.38 (d, J=17.3 Hz, 1H), 3.97 (m, 2H), 3.85 (d, J=9.5 Hz, 1H), 3.64 (t, J=8.9 Hz, 1H), 3.53 (d, J=9.5 Hz, 1H), 3.37 (s, 3H), 3.13 (d, J=9.5 Hz, 1H), 2.73 (m, 1H), 2.36-2.29 (m, 3H), 2.18 (m, 1H), 1.78 (s, 3H), 1.67 (s, 3H), 0.92 (d, J=6.8 Hz, 3H); $^{13}C$ NMR (CDCl$_3$, 125 MHz): δ 172.7, 139.8, 136.8, 133.3, 133.1, 126.9, 122.3, 89.9, 83.4, 71.4, 66.5, 65.5, 56.2, 37.2, 33.0, 29.1, 22.8, 16.6, 12.9; HRMS (ESI) calcd for $[C_{19}H_{30}O_5+Na]^+$: 361.1991. found: 361.2000.

REFERENCES

1. Aubert, C.; Begue, J. P.; Charpentier-Morize, M.; Nee, G.; Langlois, B. General method of preparation of trifluoromethyl ketones. Part I. Direct alkylation of ethyl trifluoroacetylacetate. *Journal of Fluorine Chemistry* (1989), 44(3), 361-76.

2. Aubert, C.; Begue, J. P.; Charpentier-Morize, M.; Nee, G.; Langlois, B. General method of preparation of trifluoromethyl ketones. Part II. Indirect alkylation of ethyl trifluoroacetylacetate. *Journal of Fluorine Chemistry* (1989), 44(3), 377-94.

Example 12

MDA231BrM2a is a human breast cancer cell line that is metastatic to the brain (Bos et al 2009). These cells stably express a triple fusion protein (thymidinekinase-GFP-luciferase) that allows detection by bioluminesce, and by immunofluorescence with anti-GFP antibodies. Cells ($5×10^5$ cells) were inoculated into the bloodstream of immunodeficient mice by intracardiac injection. Carboxymethyl-Migraether (cME) was administered (20 mg/kg, intraperitoneally) at days 0, 3 and 5 after injection. Mice were sacrificed 7 days after inoculation. Brains from these mice were serially sectioned (80 m sections). Anti-GFP immunofluorescence was performed and the number of GFP(+) cells (events) per brain quantified (FIG. 1). The results establish that extravasation of these cancer cells through the blood-brain barrier (BBB) occurs during the first 7 days after inoculation. Therefore, in the experiment of FIG. 1, cME targets cells during the extravasation step. A two-fold reduction in the number of events per brain was observed in cME treated animals (FIG. 1). The results indicate that the cellular target of cME mediate cancer cell migration through the BBB.

Figure 2:
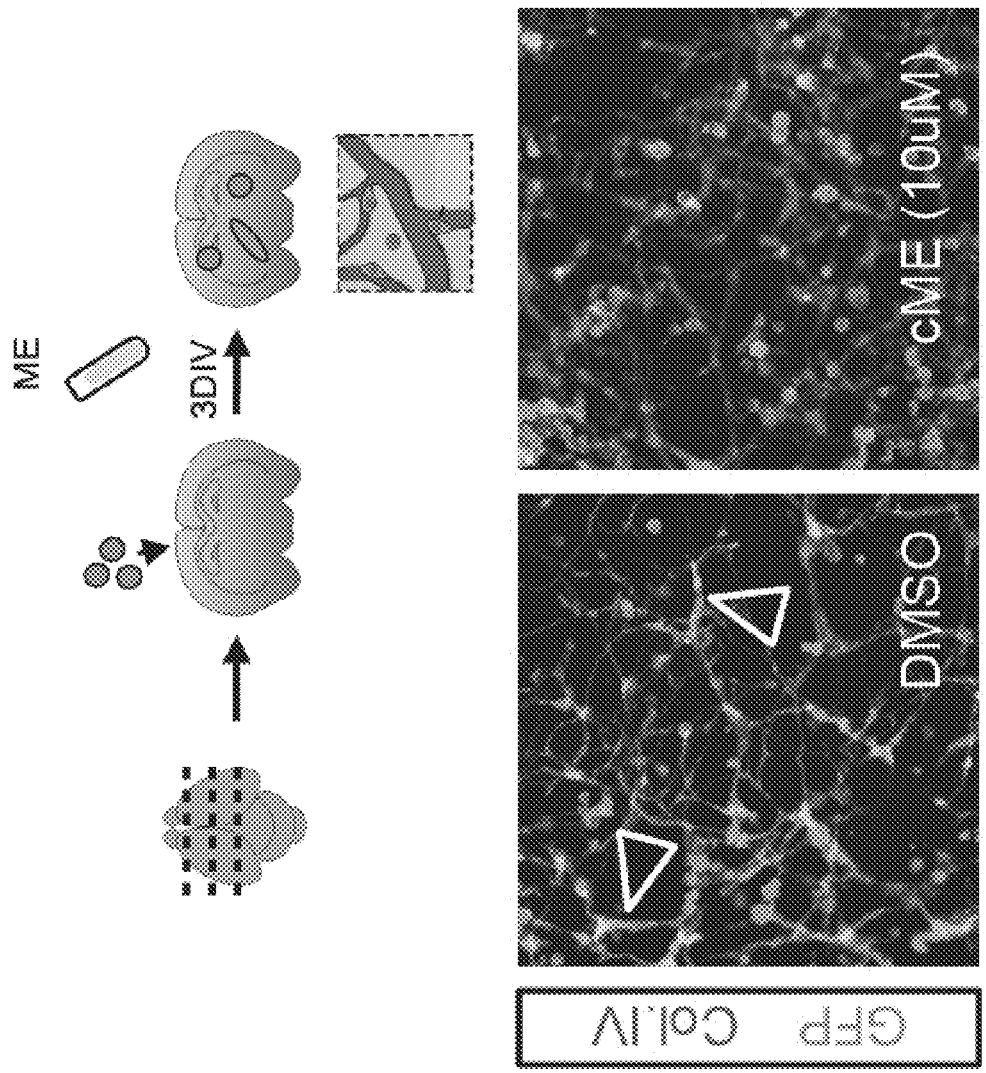
FIG. 2 depicts effects of cME on the migration of cancer cells (GFP) into a brain slice and over the capillary network (Col.IV). Experimental protocol (top) and results (bottom). Fluorescence microscopy images were obtained after 3 days of incubation, from the top surface of the brain slices.

After extravasation through the BBB, cancer cells adhere to and migrate on the surface of brain capillaries. Prior to the present disclosure, the permeability of the BBB to cME was unknown. To investigate the ability of cME to inhibit cancer cell migration over capillaries once the cells have infiltrated the brain, we used an ex-vivo intra-brain migration assay. Brain slices from untreated mice were placed in organotypic cultures. Each slice was placed on an inertporous membrane over cell culture medium. MDA231BrM2a cells ($3×10^4$ cells) were plated on top of the brain slices (FIG. 2, top). After 3 days, the cancer cells had infiltrated the brain tissue mass, migrated towards capillaries (Col. IV in FIG. 2) and migrated on the capillary network of the tissue slice (FIG. 2, bottom). Addition of 1 μM or 10 μM cME strongly inhibited these migration processes. In the presence of cME, the cancer cells remained round and on the surface of the brain slice, without migrating towards and over the vascular network (FIG. 2, bottom right).

This surprising finding indicates that cME is a strong inhibitor of migratory processes that allow human metastatic breast cancer cells to egress from the circulation through the BBB, and to subsequently migrate towards, and along the abluminal surface of blood capillaries in the brain.

Example 13

Figure 3:
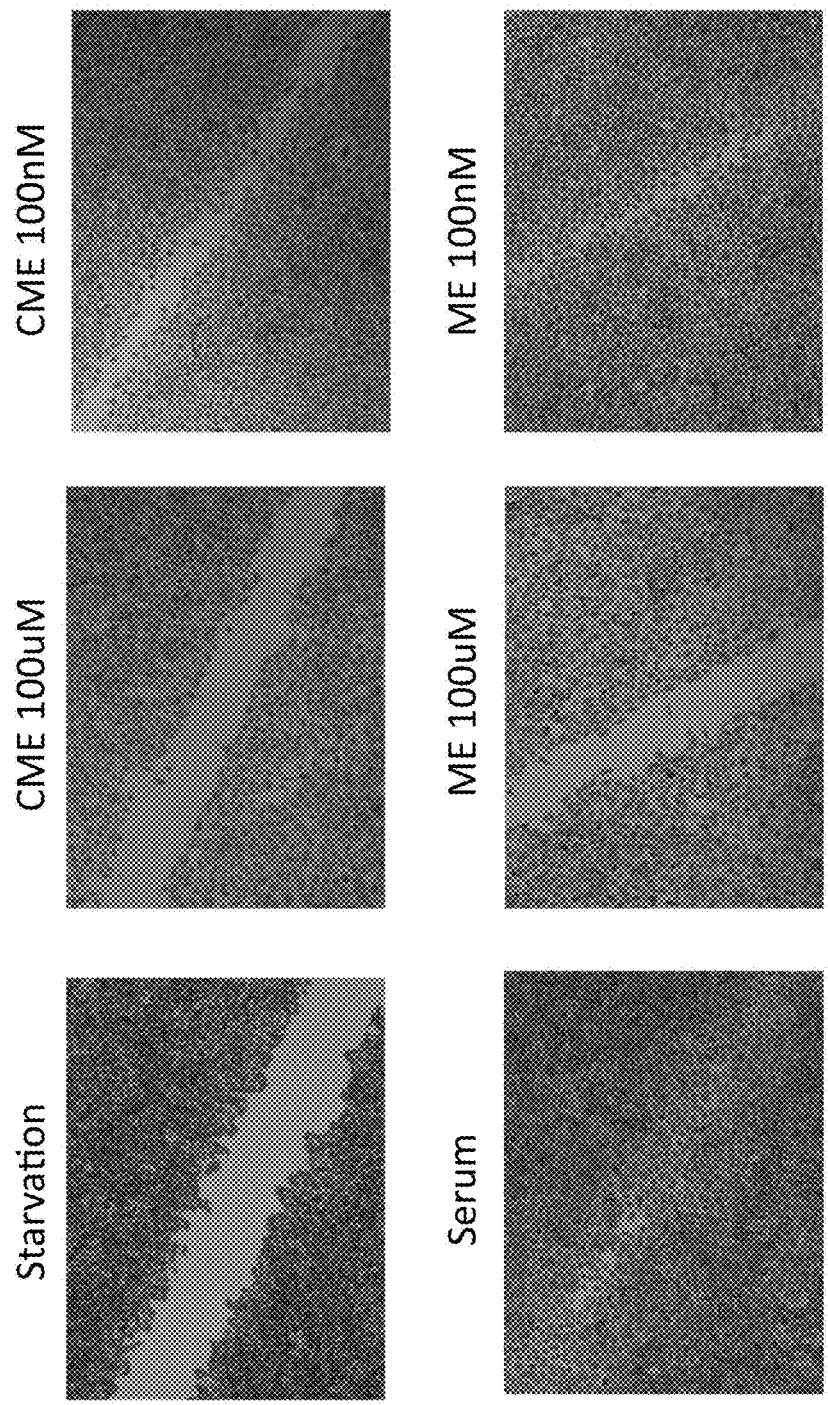
FIG. 3 depicts inhibition of A549 lung cancer cell lines migration in an in vitro wound-healing assay by migrastatin ether (ME) and carboxymethyl-migrastatin ether (cME)

This Example evaluates the anti-metastatic properties of new migrastatin analogs by assessing their ability to inhibit in vitro cancer cell migration in a wound-healing assay and their chemotaxis in a transwell migration assay. As shown in FIG. 3, Migrastatin Ether (ME) and Carboxy-Methyl Migrastatin Ether (CME) at 100 μM almost completely blocked the migration of human non-small cell lung cancer (NSCLC) A549 cells in response to a scratch wound. At submicromolar concentrations, CME compound was still quite effective (32% inhibition of migration). Similar results were obtained with a panel of human lung cancer cell lines (H1975, H647, H522, H1703, data not shown).

Migration assay: Cancer cell chemotaxis was performed towards a serum gradient in a modified Boyden chamber consisting of a cell culture insert (6.4 mm diameter, 8-μm pore polyethylene tetraphtalate membrane, [Becton Dickenson]) seated in each well of a 24-well companion plate (Becton Dickinson). Briefly, cancer cells were grown as subconfluent monolayer cultures then starved for 36 hours in serum-free M5 medium. After detachment and dissociation with 5 mM EDTA, single-cell suspensions were prepared by filtration through a 35 μm mesh cell strainer (Becton Dickinson). Cells were counted and a total of $10^5$ cells suspended in serum-free medium were seeded into the upper chamber of an insert, then positioned in a 24-well plate, containing medium with or without 10% serum. When used, drugs or DMSO (vehicle) were added to the medium at 0.2% in both chambers. Migration assays were carried out for 12 hours in a humidified incubator at 37° C. with 5% $CO_2$. Cells were then fixed with 3.7% formaldehyde, permeabilized with ice cold methanol and stained with a 0.2% Crystal violet solution. Non-migratory cells on the upper side of the insert were removed with a cotton swab. For quantification, three randomly selected fields on the lower side of the insert were photographed at 4× and 20× magnification using computer-assisted microscopy, and analyzed with CellProfiler2.0 cell image analysis software). The migration in response to the test condition was calculated relative to the DMSO vehicle control.

For the results depicted in FIG. 3, A549 cancer cells were grown as nearly confluent monolayer culture and then starved overnight in medium containing 0.5% FCS. Cell monolayers were then scratched using pipette tip, photographed, and incubated with a 6 log-scaled concentration range of ME and CME from $10^{-3}$ to $10^{-8}$M, with or without 2% FCS. After 12H, areas were fixed, stained and photographed using computer-assisted microscopy. Micrographs (4× magnification) are presented, showing the A549 cancer cell migration across the scratches in absence of serum (no migration), presence of serum (migration), and in the presence of serum plus CME or ME at 100 μM or 100 nM.

Wound-Healing Assay: Cancer cells migration was measured using an "in vitro wound-healing assay" (or scratch assay) performed in a 12-well plate (Becton Dickinson). Briefly, cancer cells were seeded at a density of 5-10×$10^4$ cells per well, grown to near confluent monolayers in 10% serum-supplemented M5 medium and then starved overnight in a low serum medium (0.5% FCS). Perpendicular wounds were scratched through the cell monolayer using a sterile 200 μL pipette tip. The cells were then washed twice very gently using PBS and the scratched areas were photographed at 4× and 20× magnification using computer-assisted microscopy. PBS was removed and replaced with 2 mL of media with or without 2% FCS, and containing drugs or DMSO (vehicle control) at 0.2% (v/v). After 12-24 hours in a humidified incubator at 37° C. with 5% $CO_2$, cells were fixed with 3.7% formaldehyde, permeabilized with ice cold methanol and stained with a 0.2% Crystal violet solution. Each well was photographed at 4× and 20× magnification and the pictures analyzed with CellProfiler2.0 cell image analysis software as previously described, (Carpenter A E, Jones T R, Lamprecht M R, Clarke C, Kang I H et al. (2006), *Genome Biology* 7(10):R100). The migration in response to the test condition was calculated as cell coverage of the original cell-free zone and related to DMSO vehicle control.

Example 14

Figure 4:
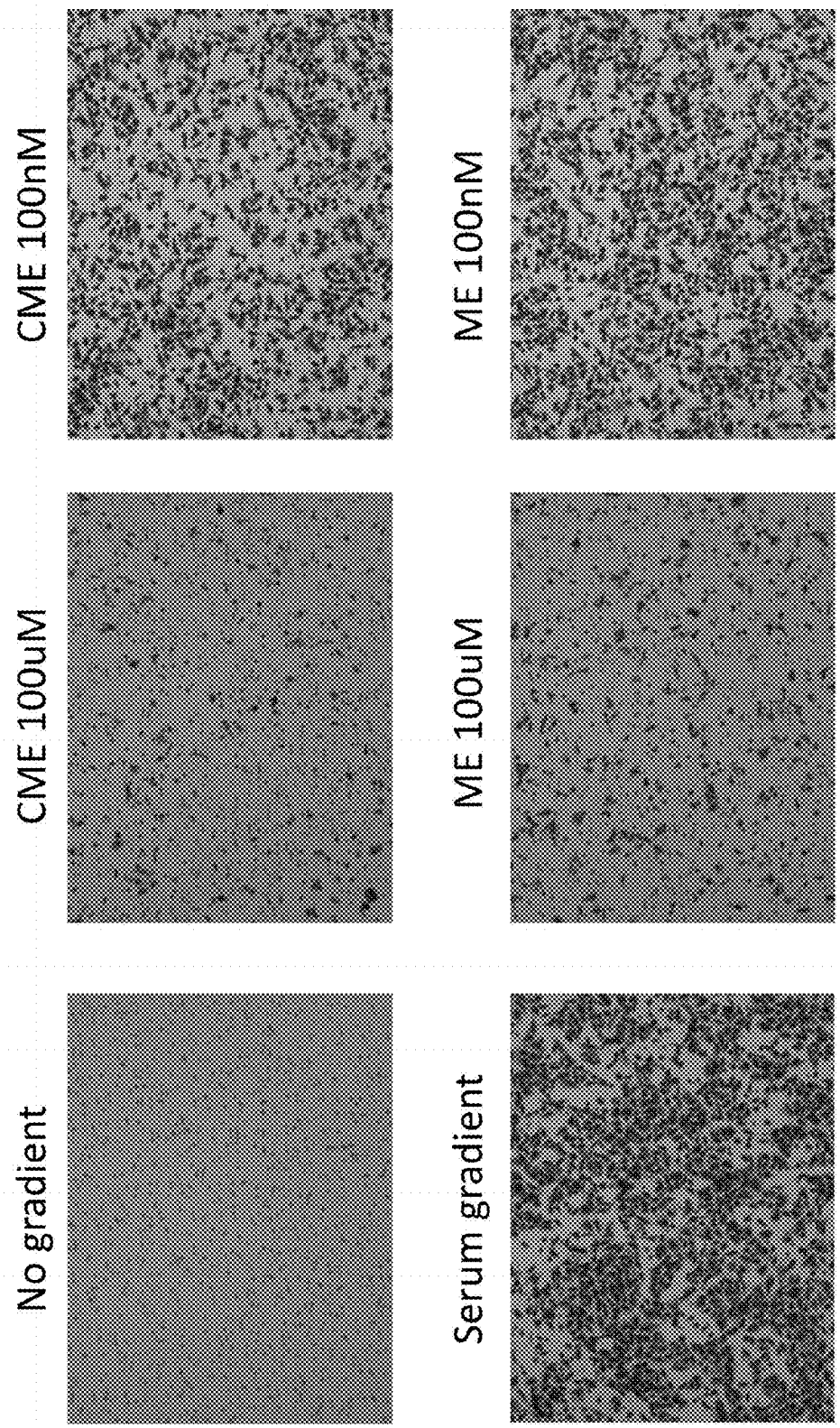
FIG. 4 depicts inhibition of trans-well lung cancer cell lines migration by migrastatin ether (ME) and carboxymethyl-migrastatin ether (CME).

This Example shows chemotaxis in response to a serum gradient in a modified Boyden chamber system to evaluate a panel of NSCLC lines. This assay provided reproducibly robust data, allowing dose-response studies to be carried out to determine the half maximal inhibitory concentration ($IC_{50}$). As shown in FIG. 4 and Table 1, migrastatin core ether analogs efficiently blocked the migration of human lung cancer cells through the 8 μm pore insert in response to the serum gradient. Comparatively, CME compound exhibits lower $IC_{50}$ values (0.5 to 5 μM) than ME compound (1.5 to 8.2 μM) respectively on A549, H1975, and H299 cancer cells. Because we noticed a mild toxicity and effects on cell proliferation in the millimolar range, experiments with CME and ME at 1 mM or more were not included for the $IC_{50}$ calculation. Collectively, these results demonstrated a very sensitive response in term of in vitro migration inhibition that was more than 2 orders of magnitude less than the concentration producing cytotoxicity.

For the results depicted in FIG. 4, cancer cell chemotaxis was performed with $10^5$ H1975 cells towards a serum gradient or in the absence of a serum gradient in a modified Boyden chamber. ME, CME or DMSO (vehicle) were added over a 10 log-scaled concentration range. Migration assays were carried out for 12 hours and cells were then fixed and stained with Crystal violet. Non-migratory cells on the upper side of the insert were removed with a cotton swab. For quantification, three randomly selected fields on the lower side of the insert were photographed at 4× and 20× magnification using computer-assisted microscopy. FIG. 4 shows results with 100 uM and 100 nM of ME or CME.

TABLE 1

Inhibition of Transwell Lung Cancer Cell lines migration by Migrastatin Ether (ME) and Carboxymethyl-Migrastatin Ether (CME)

| | IC50 (μM) | |
|---|---|---|
| Cell line | ME | CME |
| A549 | 1.93 ± 0.41 | 0.66 ± 0.20 |
| H1975 | 1.51 ± 0.69 | 0.51 ± 0.42 |
| H299 | 8.20 ± 1.75 | 5.02 ± 1.13 |

Lung Cancer cell lines chemotaxis was performed in cell culture inserts after serum starvation and an overnight preincubation with an incremental logarithmic scale of drug concentration (ME and CME from $10^{-3}$ to $10^{-10}$ M). Cancer cell migration in response to a serum gradient was measured after a 12 hour-long incubation in presence of different concentrations of ME or CME in both upper and lower chamber (three wells at each dose). Cells were then fixed and stained with Crystal violet, and photographed. Data show the half maximal inhibitory concentration (IC50, in μM) for ME and CME for A549, H1975 and H299 lung cancer cells. Data are expressed as the mean+/−SEM of three independent experiments. Each experiment was performed in triplicate.

Cells And Primary Tumor: Human Non-Small Cell Lung Carcinoma (NSCLC) cell lines were obtained from the American Type Culture Collection (Manassas, Va.) or the National Cancer Institute: NCI-A549, NCI-H1975, NCI-H299, NCI-H1993 and NCI-H1373 (Adenocarcinoma), NCI-H647 and NCI-H1703 (Squamous Cell Carcinoma of the lung [SCC]). Human primary small cell lung carcinoma (SCLC) cells, transduced with thymidine kinase/green fluorescent protein/luciferase triple fusion gene and named AC3-TGL, were previously described (Rodina A, Vilenchik M, Moulick K, Aguirre J, Kim J et al. (2007), *Nat Chem Biol August;* 3(8):498-507). All lung cancer cell lines were grown in M5-medium consisting of DME:F12 supplemented with 6 g/L Hepes, 2.2 g/L Sodium bicarbonate. Primary SCLC cells were grown in RPMI supplemented with 25 mM Hepes, 1.5 g/L Sodium Bicarbonate and 4.5 g/L Glucose (Media Preparation Core Facility, MSKCC). Both media were supplemented with 10% (v/v) fetal calf serum, 2 mM L-Glutamine and 500 U/mL penicillin and streptomycin.

Proliferation Assay: Cells are plated in flat-bottom 96-well plates at a density of $5 \times 10^3$ cells per well in 150 μL of complete medium. When used, drugs or DMSO (vehicle) are added to the medium at 0.2%. After 3 and 6 days of treatment, cell proliferation is assessed by adding CellTiter 96 AQueous Assay reagent (Promega) to each well according to the manufacturer's instructions. After 2-hour incubation at 37° C., cell proliferation is determined by measuring the absorbance at 490 nm, using a 96-well plate reader.

Example 15

Figure 5A:
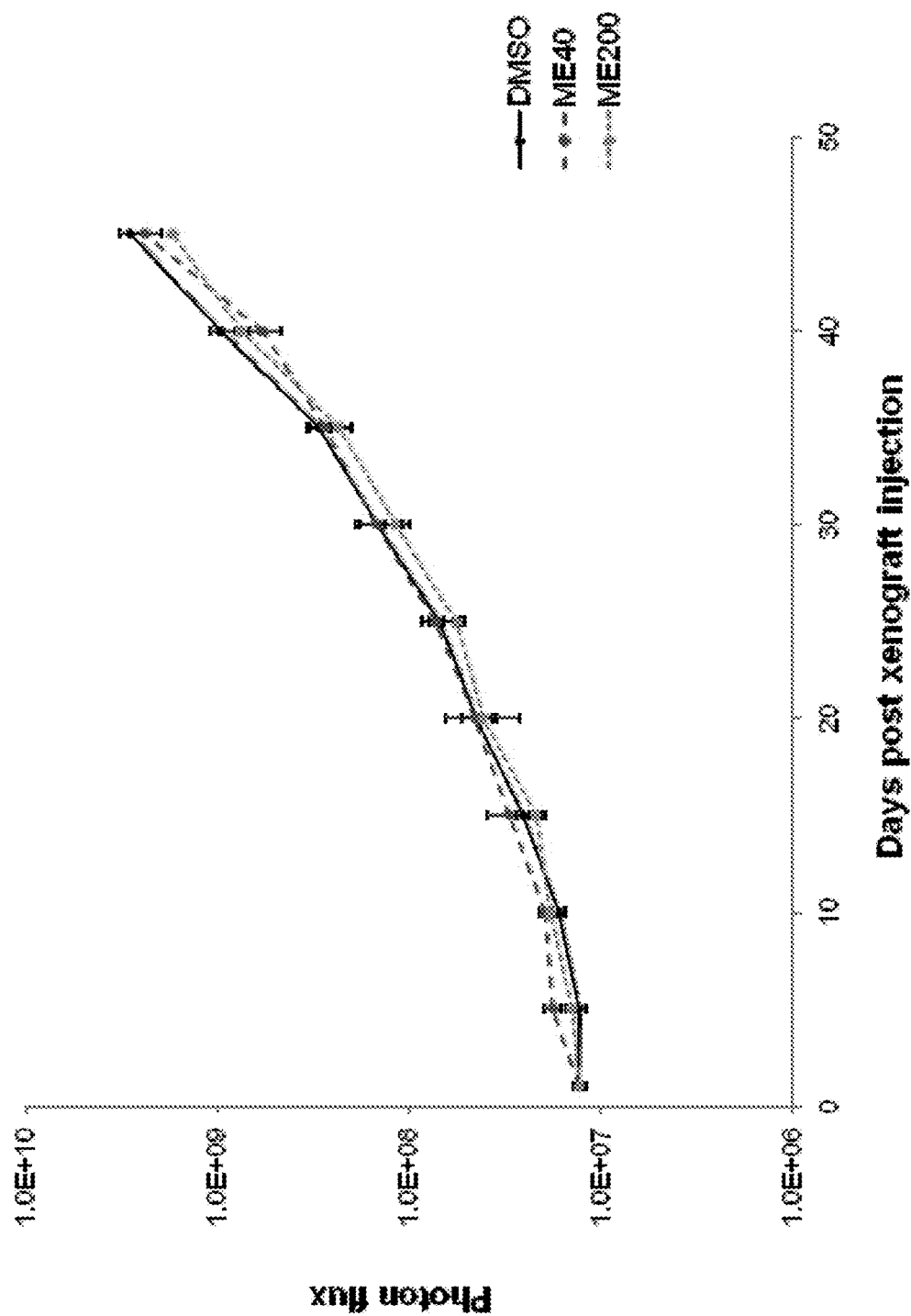
FIGS. 5*a-c* depicts ME inhibition of metastasis in a human primary SCLC xenograft model.
Figure 5B:
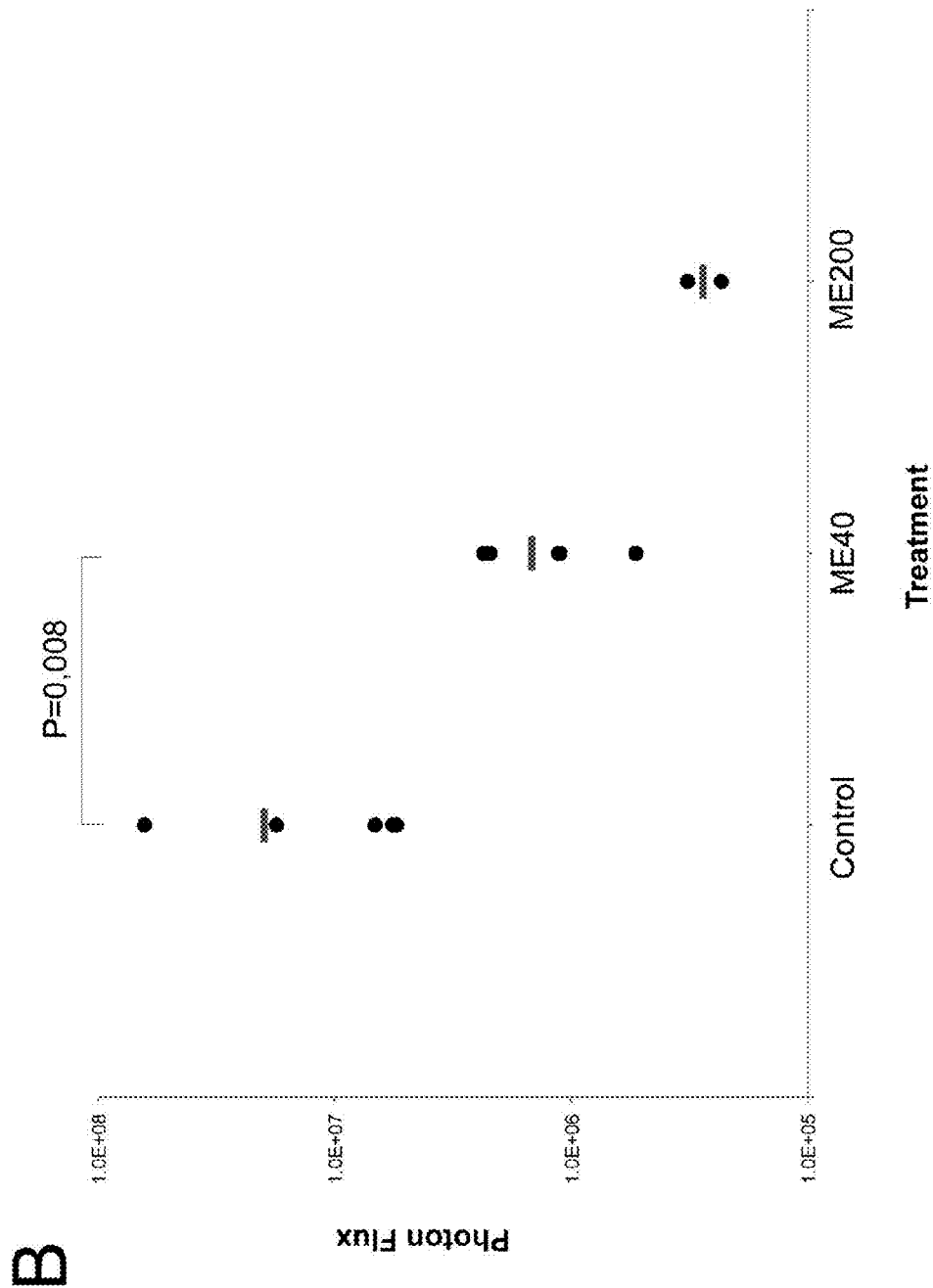
Figure 5C:
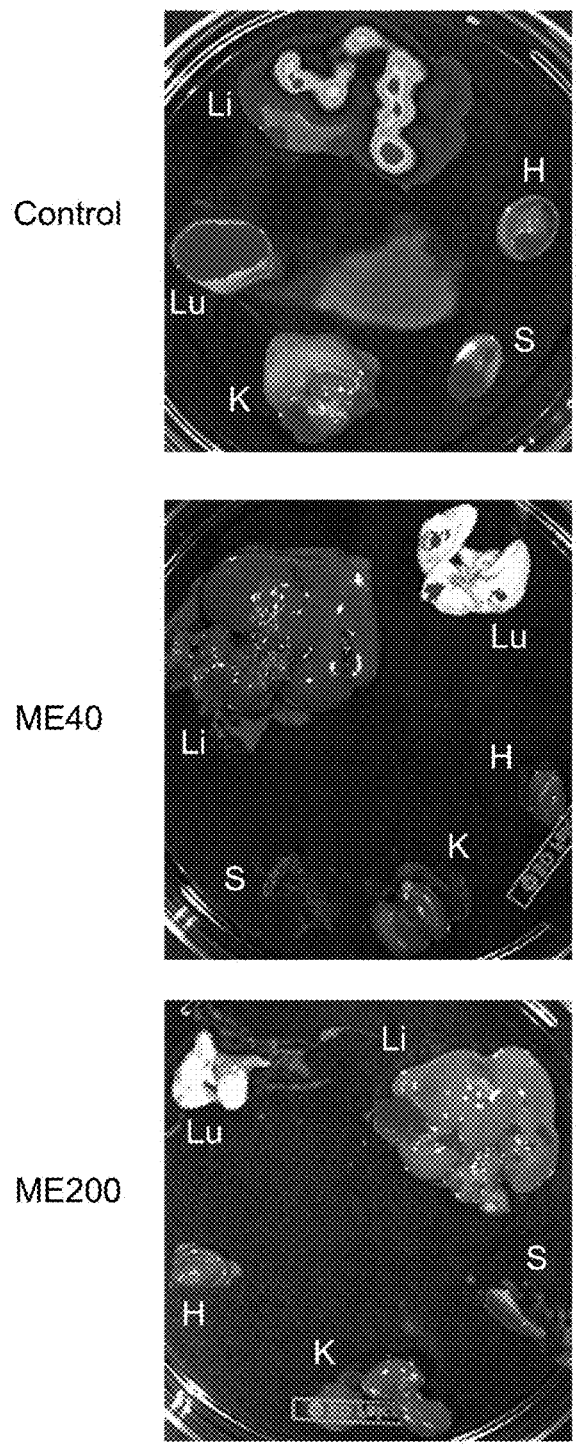

This Example studied whether the ME analog affects tumor metastasis in a human small cell lung cancer (SCLC) primary xenograft model. These cells in primary and subsequent in vivo passages in NOD-SCID mice formed liver metastases. The tumor cells were stably transduced with a triple-fusion protein reporter construct (AC3-TGL), and were transplanted by subcutaneous injection with matrigel into NOD/SCID IL2R gamma null (NSG) mice. Started 1 day prior the inoculation of tumor cells, ME treatment was initiated by intraperitoneal injection at 40 mg/kg (ME40) or 200 mg/kg (ME200) three times a week in groups of 5 mice. Control mice were treated with DMSO vehicle. Tumor burden and metastatic spread were monitored every 5 days by serial non-invasive bioluminescent imaging. As shown in FIG. 5a, drug treatment did not significantly interfere with tumor growth kinetics at the primary site of injection. In contrast to the control and ME40-treated groups, a toxicity was observed with the highest dosage (ME 200 group) and 3 mice died before the endpoint. However no body-weight loss, lethargy or other obvious side effects were noticed for the 2 surviving mice after 45-days of ME treatment. At the endpoint, the potential metastatic sites (liver, lung, spleen, heart and kidney, gastrointestinal tract) were surgically resected and the luciferase activity quantified by ex-vivo bioluminescence imaging (FIG. 5b). Compared to the control, the treated group with low dose ME (40 mg/kg), exhibits a significant decrease in term of overall metastasis (93%, p-value=0.008) (FIG. 5c). An even greater degree of metastasis inhibition (99%) was seen in the 2 surviving mice treated with high dose ME (200 mg/kg). Bioimaging of mice after removal of the various organs showed no other metastatic sites. These results indicate that ME is a potent in vivo inhibitor of metastasis for small cell lung cancer, and it is expected that similar analogs (e.g., compounds of formula I) will have similar activity.

For the results depicted in FIGS. 5a-c, AC3-TGL cells were transplanted by subcutaneous ventral injection into NSG mice. Xenografted mice were treated with indicated dosages of ME every 3 days started from day −1 after tumor inoculation: 40 mg/kg (ME40, n=5), 200 mg/kg (ME200, n=5)) and DMSO vehicle (Control, n=5). At day 45, the mice were sacrificed. Three mice in the ME200 group died before the end of treatment, at day 23, 30 and 34. (A) Tumor growth. Every 5 days, the tumor burden was monitored by in vivo Bioluminescence Imaging (BI) and data is expressed as photon flux (flux in photon/sec)+/−SEM in log scale. (B, C) Tumor metastasis at endpoint. At day 45, mice were analyzed for metastasis by ex vivo BI quantifying luciferase activity in the excised lungs (Lu), liver (Li), heart (H), kidneys (K) and the spleen (S). Measurements for each mouse are presented on the panel B (circles), with the average per group (short line) and expressed as photon flux (flux in photon/sec) in log scale. P-values were obtained using two-tailed Mann-Whitney U-test. Pictures of bioluminescence signal measured on the organs from 1 mouse of each group are presented on the panel C. Each picture is presented with the same settings (4 min exposure; photon signal; color scale from 5.E6 (min) to 1.E8 (max)).

Xenograft Model for Example 15: A human primary SCLC xenograft model was developed in 10-14 weeks old male non-obese diabetic severe combined immunodeficient (NOD/SCID) Interleukin-2 gamma Chain Receptor Null Mice (NSG). Primary tumor samples were obtained after patient informed consent. AC3-TGL primary cells growing as clumps were processed into a single-cell suspension by Trypsin/Collagenase IV (Invitrogen) sequential treatment and filtrated as described above. Xenografts were performed by subcutaneous ventral injection of $10^3$ AC3-TGL cells in serum-free medium mixed with Matrigel (Becton Dickinson). One day prior to the tumor cell injection, mice were pretreated with Migrastatin Ether (ME) compounds at a dose of either 40 mg/kg or 200 mg/kg per mouse or with DMSO vehicle control (n≥5 mice per group). Drug treatment was delivered by intraperitoneal injection every 3 days started from day −1 after cell injection to day 45. During this time, the tumor burden and metastatic spread were monitored by bioluminescence imaging (BLI) every 5 days. At day 45 (endpoint), the mice were killed and the metastatic spread of tumor cells to the lungs, liver, heart, kidneys, spleen and GI tract was assessed by ex-vivo BLI on the removed organs.

Example 16

Trans-Well Cell Migration Assay

Figure 6:
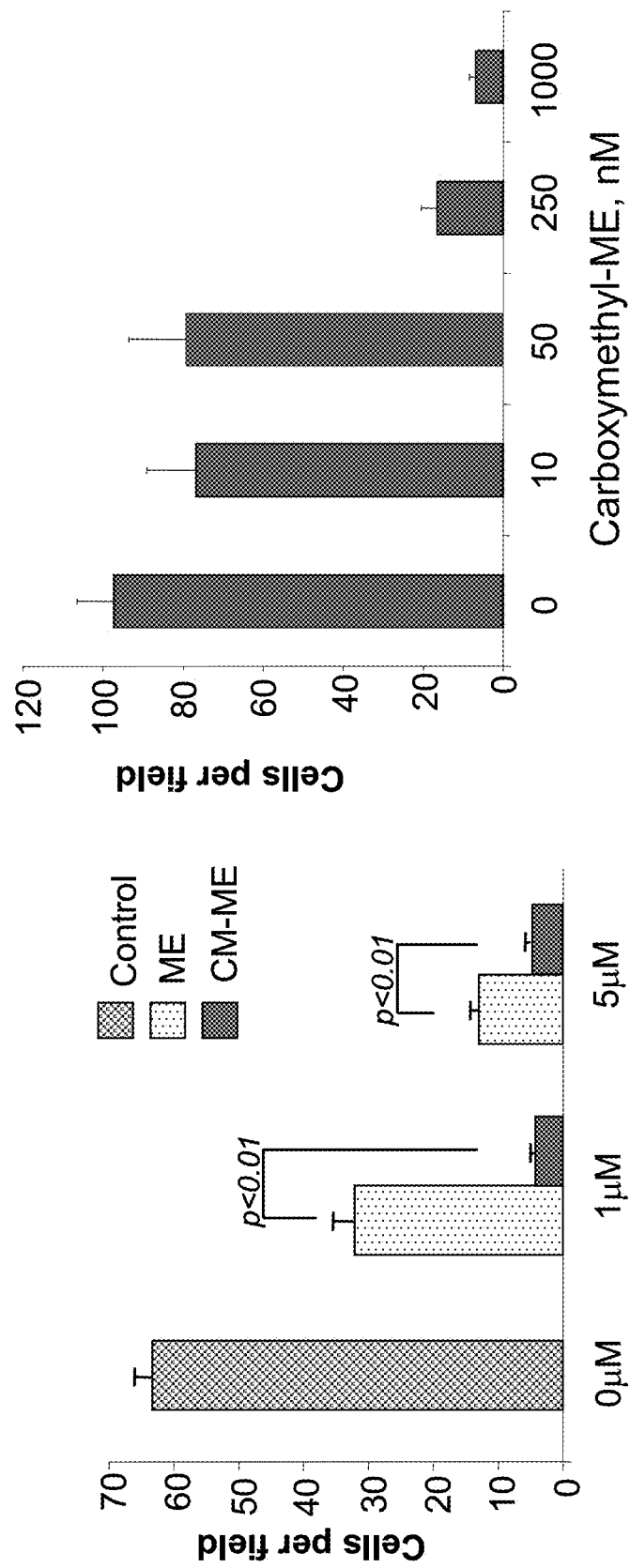
FIG. 6 depicts the effects of ME and cME on metastatic breast cancer cells in a trans-well cell migration assay.

MDA231-LM2 lung metastatic breast cancer cells were pre-treated with the indicated concentrations of ME or Carboxymethyl-ME for 24 hours. Following the pre-treatment, migration was determined using a Boyden chamber with 3 μm pore size filters. Cells were allowed to migrate for 5 hours through the chamber (in the presence of ME or Carboxymethyl-ME). Cells that traversed the porous membranes were analyzed and scored under a fluorescence microscope. CM-ME is approximately 20-fold more potent than ME at inhibiting the restrictive migration of breast cancer cells. The results are expressed as transmigrated cells per optical field. Data are averages of triplicates±S.D. (See FIG. 6)

Example 17

Evaluation of the anti-metastatic activity of ME (19) and CME (25) in a human SCLC xenograft model. These cells, in primary and subsequent in vivo passages in NOD/SCID mice, tend to form liver metastases. The tumor cells were stably transduced with a triple-fusion protein reporter construct (AC3-TGL), and then transplanted by subcutaneous injection with matrigel into NOD/SCID IL2R gamma null (NSG) mice.

Starting 1 day prior to the inoculation of tumor cells, groups of mice were treated with ME at doses of 10 mg/kg, 40 mg/kg, or 200 mg/kg, or with CME at 12 mg/kg or 49 mg/kg (note: dosage levels were adjusted to account for differences in molecular weight: 1 mg ME=1.2 mg CME).

Control mice were treated with DMSO vehicle. The compounds were administered by i.p. injection every three days, from Day −1 to Day 55 following cell injection (n≥5 mice per group). During this time, tumor burden and metastatic spread were monitored by serial non-invasive bioluminescent imaging (BLI) at Days 14, 23, 30, 40, and 50. At Day 55, the mice were sacrificed and the metastatic spread of tumor cells to the lungs, liver, heart, kidneys, and spleen was assessed by ex-vivo BLI on the removed organs.

Treatment with ME and CME did not significantly affect tumor growth kinetics at the primary site of injection. In the ME-treated cohorts, some toxicity was observed, resulting in the deaths of 3 mice in the 200 mg/kg group and 2 mice each in the 10 mg/kg and 40 mg/kg groups prior to the study endpoint. In contrast, no toxicity was observed in either cohort of CME-treated mice.

TABLE 2

Inhibition factors of overall metastasis by ME/CME treatment

| Group | IF[a] |
|---|---|
| ME10 | 96.2 |
| ME40 | 99.1 |
| ME200 | 99.8 |
| CME12 | 99.3 |
| CME49 | 99.8 |

[a]Inhibition factors (IF) represent the percentage of reduction of overall metastasis at the endpoint, calculated after the quantification of the luciferase activity in the resected organs (liver, lungs, spleen, heart and kidneys) by ex-vivo bioluminescence imaging, reported to the control.

Figure 7A:
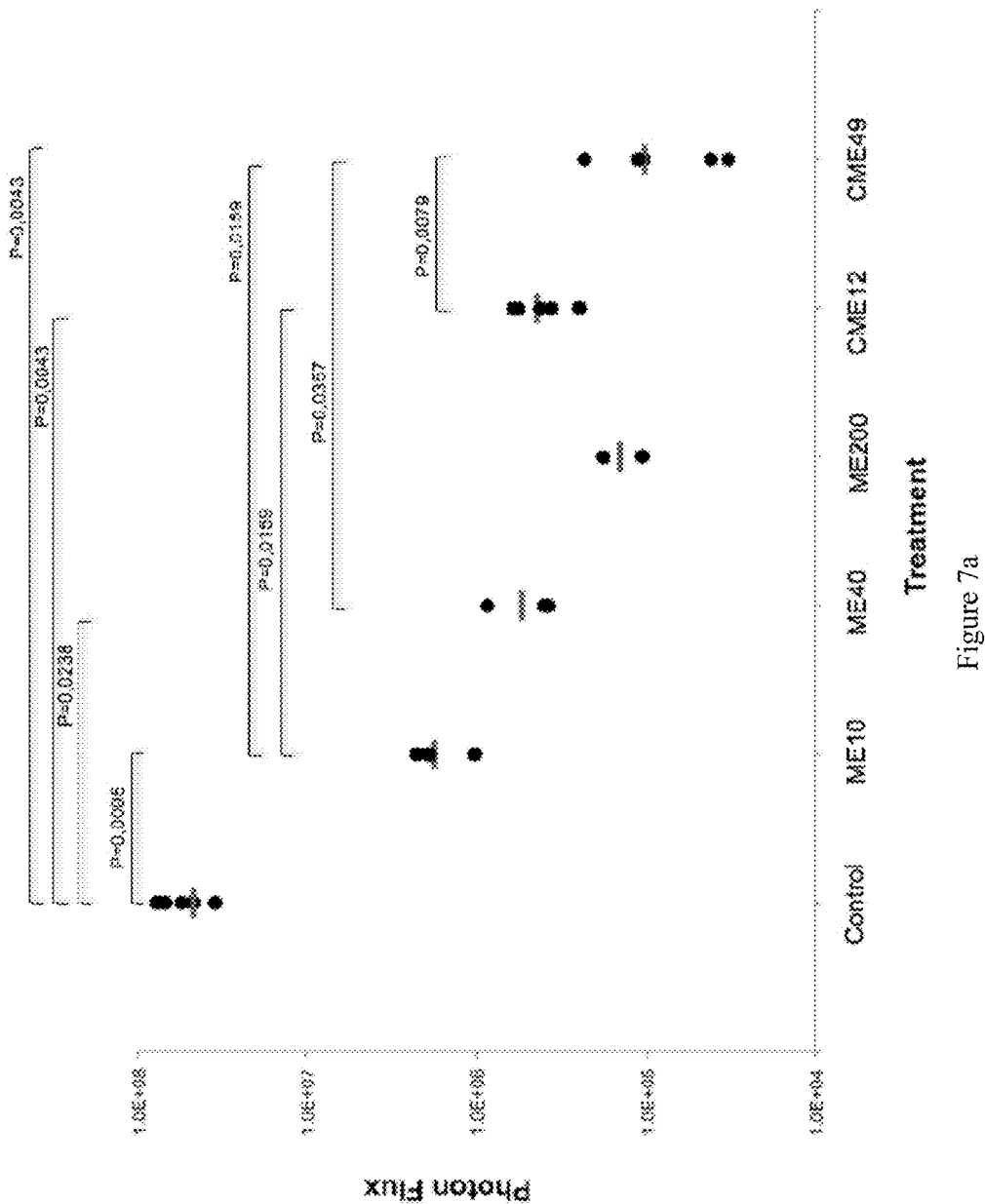
FIGS. 7*a-b* depicts a comparison of CME and ME for inhibition of metastasis in a human primary xenograft model.

At the study endpoint, the potential metastatic sites (liver, lungs, spleen, heart, and kidneys) were surgically resected and the luciferase activity quantified by ex-vivo BLI. Compared to the control group, the mice treated with 10 mg/kg or 40 mg/kg ME exhibited significantly decreased levels of overall metastasis, with calculated inhibition factors of 96.2% (p-value=0.0095) and 99.1% (p-value=0.0043), respectively (FIG. 7a and Table 2). An even greater degree of metastasis inhibition (99.8%) was seen in the 2 surviving mice treated with high dose ME (200 mg/kg). Bioimaging of mice after removal of the various organs showed no other metastatic sites.

The CME analog was found to be significantly more potent than the parent compound, ME, in inhibiting in vivo tumor metastasis. Thus, as shown in FIG. 7a, treatment with low-dose CME (12 mg/kg) led to suppression of metastasis by 99.3%, rendering CME approximately 4 times more potent than ME at the lowest dosage level. Moreover, at 49 mg/kg, tumor metastasis was inhibited by 99.8%. These findings, which are consistent with in vitro results, lend support to Applicant's hypothesis that appendage of a carboxymethyl functionality onto the ME scaffold provides enhanced migratory inhibition activity. Such activity is characteristic of chemotherapeutics useful for the treatment of tumor metastasis.

Applicant has identified herein compounds that are inhibitors of metastasis. While not wishing to be bound by any particular theory, the current data indicate the compounds do not appear to attack the primary tumors, but one could readily imagine considerable clinical benefits from an agent which blocks metastasis. Applications of an anti-metastatic agent could be particularly helpful following resection of the primary tumor via surgery, chemotherapy, or radiation.

Figure 7B:
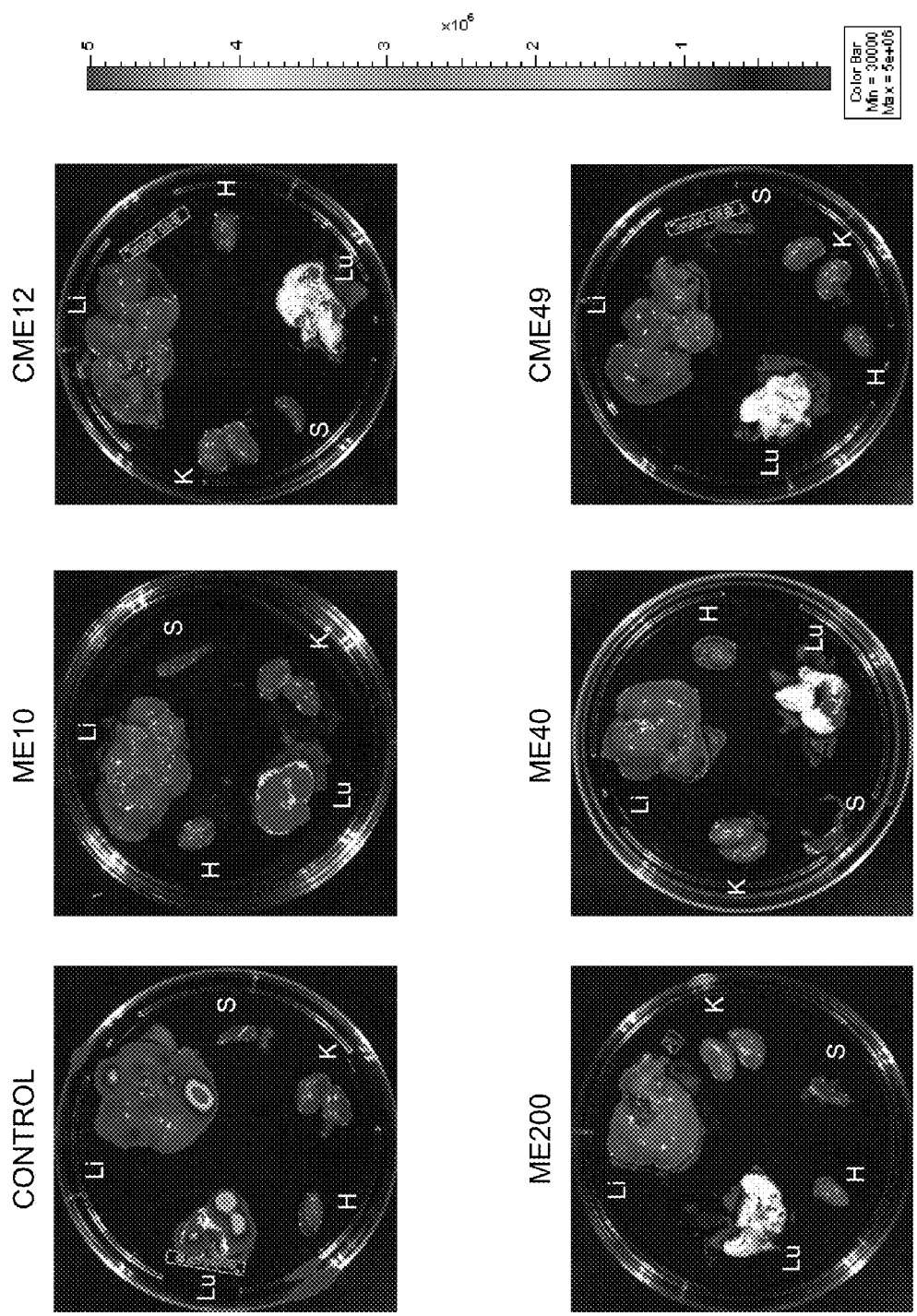

For the results depicted in FIGS. 7a-b: AC3-TGL cells were transplanted by subcutaneous ventral injection into NSG mice. Xenografted mice were treated with indicated dosages of CME or ME every 3 days starting 1 day prior to the inoculation of tumor cells: ME 10 mg/kg (ME10, n=5), 40 mg/kg (ME40, n=5), 200 mg/kg (ME200, n=5), CME 12 mg/kg (CME12, n=5), 49 mg/kg (CME49, n=5) and DMSO vehicle (control, n=6). At day 55, the mice were sacrificed. Three mice in the ME200 group died before the end of treatment. Tumor metastasis at endpoint: At day 55, mice were analyzed for metastasis by ex vivo BLI quantifying luciferase activity in the excised lungs, (Lu), liver (Li), heard (H), kidneys (K), and the spleen (S). Measurements for each mouse are presented in FIG. 7a (circles), with the average per group (short line) and expressed as photon flux (flux in photon/sec) in log scale. P-values were obtained using two-tailed Mann-Whitney U-test. Pictures of bioluminescence signal measured on the organs from one mouse of each group are presented in FIG. 7b. Each picture is presented with the same settings (4 min exposure, photon signal, color scale from $3.10^4$ (min) to $5.10^6$ (max)).

Xenograft Model for Example 17: A human primary SCLC xenograft model was developed in 10-14 weeks old male NSG mice. Primary tumor samples were obtained after patient informed consent under an MSKCC IRB approved protocol. AC3-TGL tumor cells growing as clumps were dissociated into a single-cell suspension by Trypsin/Collagenase IV (Invitrogen) sequential treatment. Xenografts were performed by subcutaneous ventral injection of 500 AC3-TGL cells in serum-free medium mixed with Matrigel (Becton Dickinson).

One day prior to the tumor cell injection, mice were pretreated with either: (1) Migrastatin Ether (ME) at a dose of 10 mg/kg, 40 mg/kg or 200 mg/kg per mouse; (2) Carboxymethyl-ME (CME) at a dose of 12 mg/kg or 49 mg/kg; or (3) DMSO vehicle control (n≥5 mice per group). Drug treatment was delivered by intraperitoneal injection every 3 days starting from day −1 after cell injection to day 55. During this time, the tumor burden and metastatic spread were monitored by bioluminescence imaging (BLI) at day 14, 23, 30, 40, and 50. At day 55 (endpoint), the mice were killed and the metastatic spread of tumor cells to the lungs, liver, heart, kidneys, and spleen was assessed by ex-vivo BLI on the surgically resected organs.

Example 18

Migration Assay

Multiple myeloma cell chemotaxis was performed towards a SDF-1α in a modified Boyden chamber consisting of a cell culture insert (4.26 mm diameter, 8-μm pore polyester membrane) seated in each well of a 96-well plate (HTS Transwell-96 System, Corning). Briefly, multiple myeloma cells were grown as subconfluent cultures then starved for 24 hours in serum-free IMDM medium. Single-cell suspensions were prepared by mechanical dissociation, then the cells were counted and a total of $5.10^4$ cells suspended in serum-free IMDM medium were seeded into the upper chamber, then positioned in a 96-well plate, containing medium with or without SDF-1α (at 200 ng/mL). To assay the inhibition of migration by migrastatin analogs, 24 hour-long starved MM cells were pretreated with drugs (5 μM and 250 μM) or DMSO (vehicle) for 8 hours, and then seeded into the insert. Migrastatin analogs or DMSO (vehicle) were added to the medium at 0.5% in both chambers. Migration assays were carried out for 6 hours in a humidified incubator at 37° C. with 5% $CO_2$. At the assay endpoint, the inserts were removed and the migrating cells were counted in the well. The migration in response to the test condition was calculated relative to the DMSO vehicle control.

Figure 8:
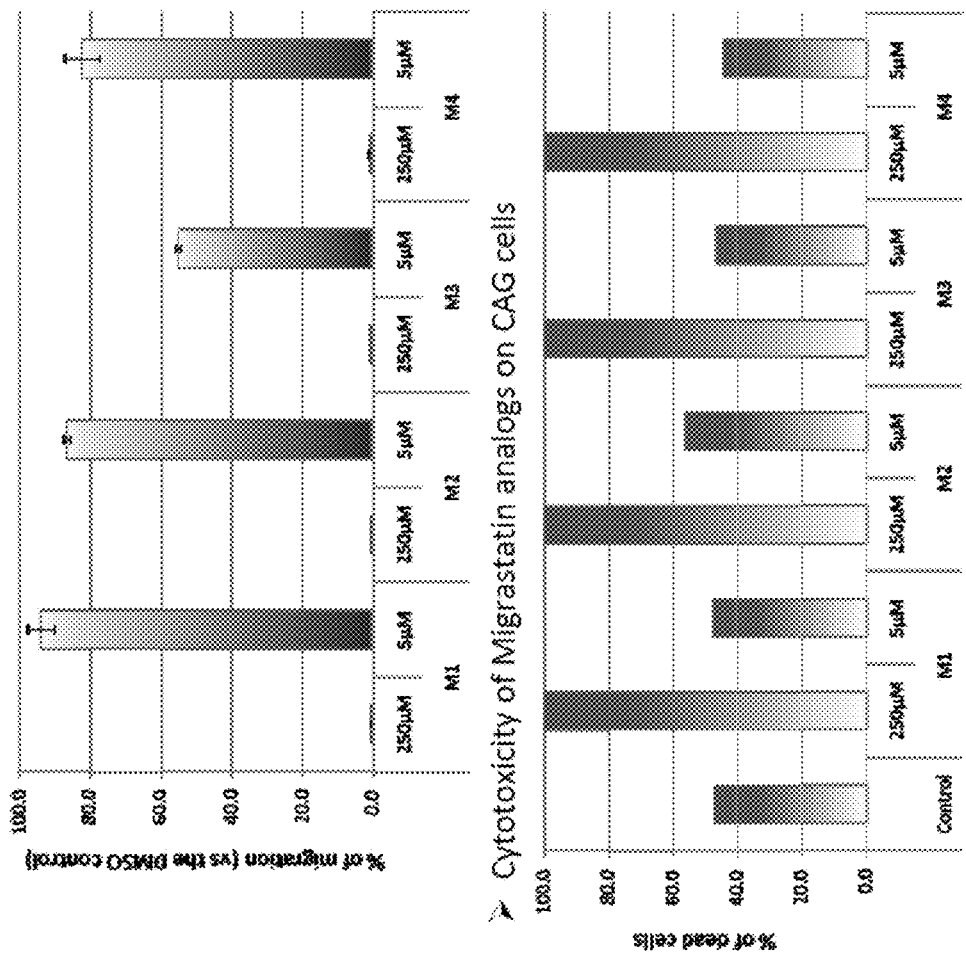
FIG. 8 depicts inhibition of migration and cytotoxicity data in CAG multiple myeloma cells for various compounds of formula I.
Figure 9:
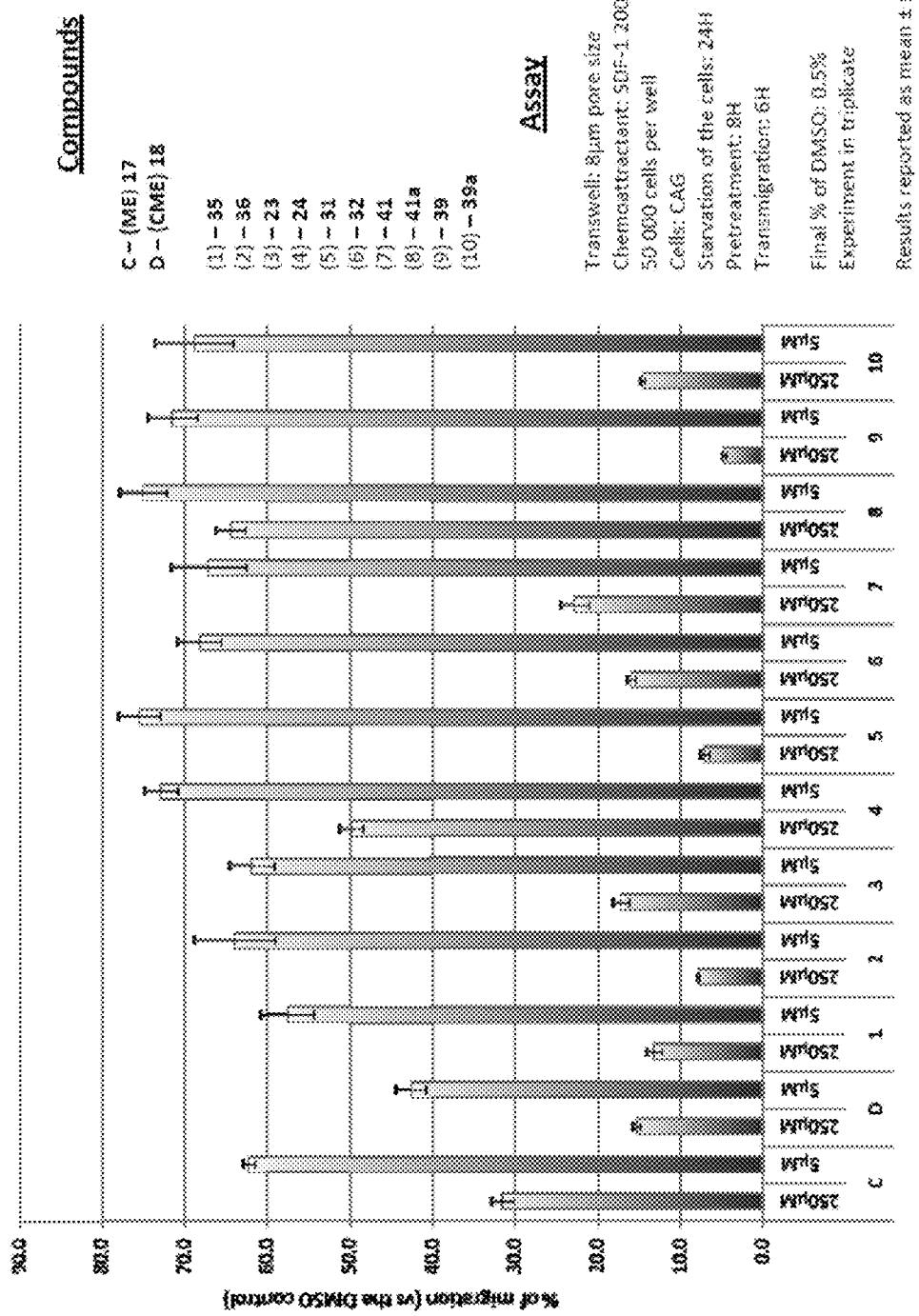
FIG. 9 depicts inhibition of migration data in CAG multiple myeloma cells for various compounds of formula I.
Figure 10:
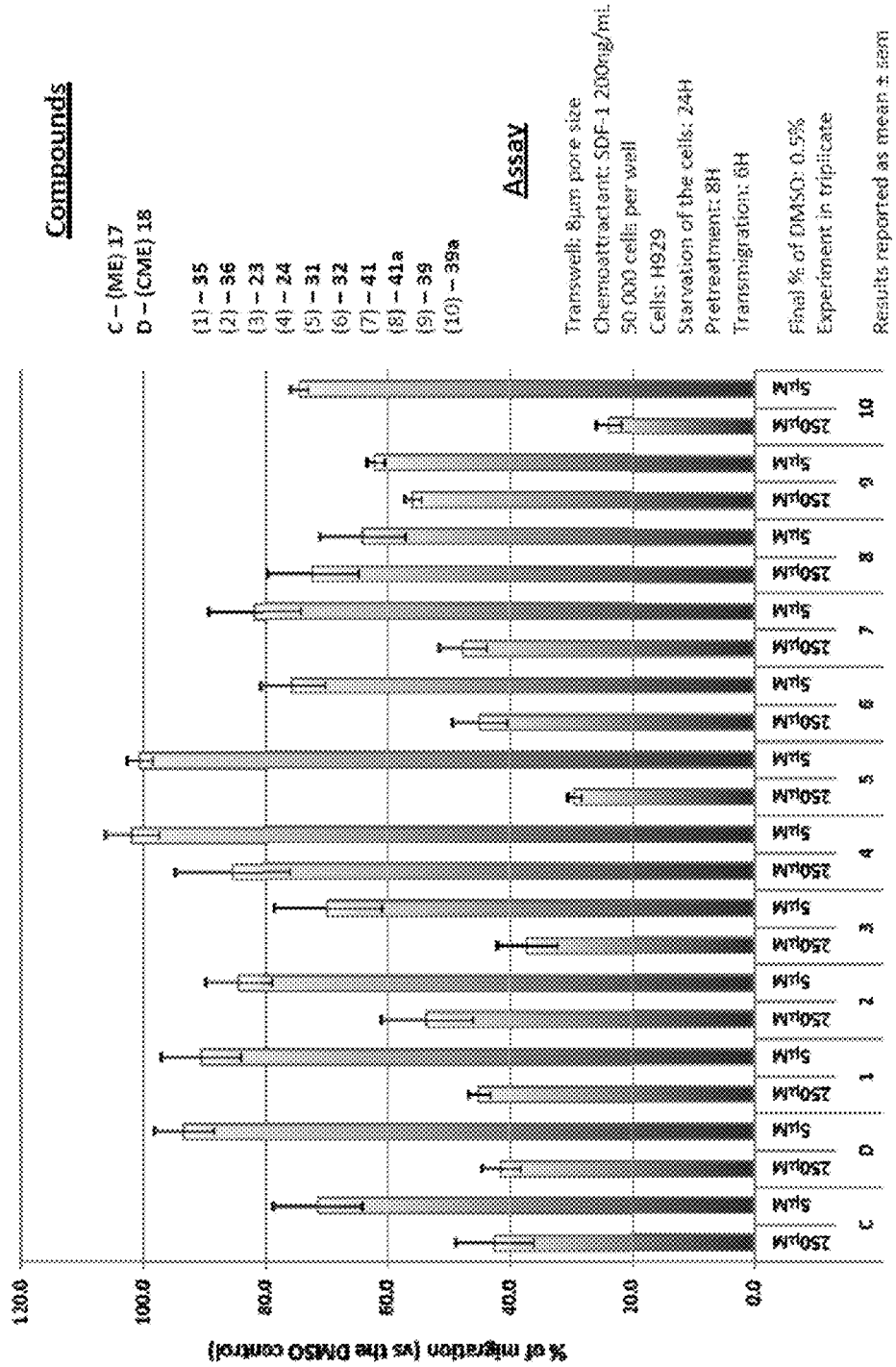
FIG. 10 depicts inhibition of migration data in H929 multiple myeloma cells for various compounds of formula I.

Table 3 and FIGS. 8-10 show the effects of certain compounds of formula I on migration in select cell lines. Unless otherwise specified, the protocol used corresponds to that in the previous paragraph.

TABLE 3

Effect of compounds 42-45 on migration of H929 and CAG multiple myeloma cells at two concentrations. The transwell assay was conducted using 8 mm pore size with SDF-1 chemoattractant (200 ng/mL) and 50 000 cells per well. Starvation time of the cells: 24 h, pretreatment time: 8 h, and transmigration time 6 h. Values reported as % of migration relative to DMSO control.

|  | 42 | | 43 | | 44 | | 45 | |
| --- | --- | --- | --- | --- | --- | --- | --- | --- |
|  | 250 µM | 5 µM | 250 µM | 5 µM | 250 µM | 5 µM | 250 µM | 5 µM |
| H929 | | | | | | | | |
| Average | 7.08 | 91.03 | 0.98 | 52.26 | 4.06 | 81.48 | 5.51 | 62.38 |
| sem | 3.92 | 3.48 | 0.41 | 5.35 | 2.32 | 5.56 | 5.25 | 5.96 |
| CAG | | | | | | | | |
| Average | 0.23 | 93.63 | 0.71 | 82.04 | 0.05 | 86.22 | 0.58 | 54.48 |
| sem | 0.08 | 3.98 | 0.04 | 5.03 | 0.01 | 1.06 | 0.11 | 0.71 |

FIG. 8 is a graphical representation of Table 3.

Example 19

Determination of Toxicity of Compounds 42-45 on Multiple Myeloma and Lung Cancer Cell Lines The toxicity of compounds 42-45 and their $IC_{50}$ was determined on a panel of human tumor cell lines of multiple myeloma (RPMI8226, MM1S, MM1R, ARP-GL, CAG-GL, OPM2-GL, SKO-007-GL, U266-GL,) and lung cancer (H299-GL, H522-GL, H647-GL, A549-GL, A549-GL, HI1993, H1075-GL, HI1373, H17030) origin. Tumor cells were dissociated into a single-cell suspension by Trypsin/Collagenase IV treatment and 500 cells per well were aliquoted into each well of 384 microwell plates in 50 µl of RPMI medium with 10% FCS. Compounds 42-45 were dissolved in DMSO and serially diluted in RPMI medium plus 10% FCS and added (1 mM to 1 nM) to quadruplicate wells containing tumor cells. Dilutions of DMSO without compound were used as a control. After 18 hrs or 2 days, the cultures were pulsed with 6 µl of alamarBlue® (Invitrogen Inc. Grand Island, N.Y.) and incubated overnight. The alamarBlue® provides a cell growth indicator based on detection of metabolic activity. The assay system incorporates an oxidation-reduction indicator that both fluoresces and changes color in response to chemical reduction of growth medium resulting from cell growth. The fluorescence intensity was measured using a Synergy H1 Microplate Reader (Biotek Inc, Winooski, Vt.) and a dose-response curve established for $IC_{50}$ determination. The data is shown in Table 4 and demonstrate indicating that the compounds 42-45 are minimally toxic and only at very high concentrations ($IC_{50}$ 300-795 µM).

TABLE 4

Estimated lethal doses (LD50) in µM for multiple myeloma (mean values from RPMI8226, MM1S, ARP-GL, CAG-GL, OPM2-GL, SKO-007-GL, U266-GL, MM1R cells) and lung cancer (mean values from H299-GL, H522-GL, H647-GL, A549-GL, H1993, H1075-GL, H1373-GL H1703 cells) measured after 18 h and 48 h exposure to compounds 42-45.

|  | Multiple Myeloma | | Lung Cancer | |
| --- | --- | --- | --- | --- |
|  | 18 h | 48 h | 18 h | 48 h |
| 42 | 515.2 | 476.4 | 741.2 | 602.7 |
| 43 | 530.8 | 406.1 | 523.9 | 510.7 |
| 44 | 182.5 | 210.6 | 299.7 | 316.7 |
| 45 | 275.6 | 217.3 | 446.9 | 446.8 |
| ME | 794.8 | 881.7 | ND | 639.8 |
| CME | 503.6 | 452.9 | 553.9 | 697.9 |

Example 20

Pharmacokinetic Studies

Groups of mix gender mice (B6D2F1) were used. Pharmacokinetics (PK) were performed on heparinized mouse plasma samples obtained typically at 0 hr, 0.17 hr, 0.5 hr, 0.75 hr, 1 hr, 2 hr, 4 hr, 8 hr, 16 hr and 24 hr after the bolus intravenous or intraperitoneal injections for CME. Samples were analyzed using a HPLC-MS/MS method. To determine the level of CME, the drug was first isolated from plasma with a sample pre-treatment. Acetonitrile were used to remove proteins in samples. An isocratic HPLC-MS/MS method was then used to separate the drugs from any potential interference. Compound levels were measured by MS detection with a multiple reaction monitoring (MRM) mode. PK data was analyzed using the WinNonlin program (ver. 5.3, Pharsight) compartmental model of analysis.

| CME, Mouse PK screening 20 mg/kg in 2% GDM-12 | $AUC_{0-24\,hr}$ (hr · ng/mL) | $AUC_{inf}$ (hr · ng/mL) | Half-life ($t_{1/2}$) | $C_{max}$ (ng/mL) | CL (mL/hr/kg) | Bioavailability (%) |
| --- | --- | --- | --- | --- | --- | --- |
| A: ip | 27814.4 | 27861.2 | 2.4 | 369 | 717.8 | 77.8 |
| B: iv | 35729.6 | 36016.4 | 2.9 | 1536 | 555.3 | — |

Figure 11:
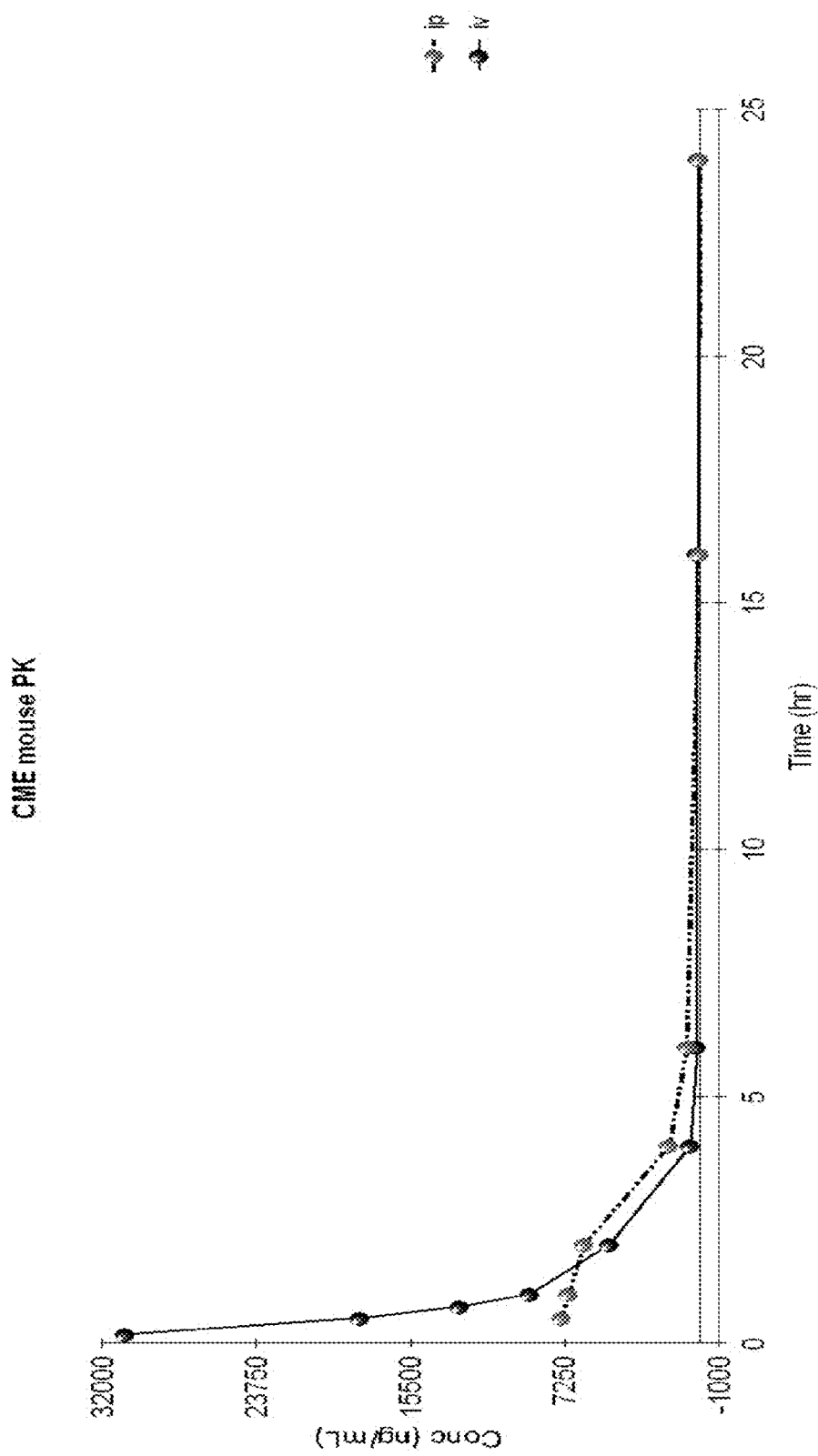
FIG. 11 depicts pharmacokinetic data for cME.

FIG. 11 shows mouse PK profiles of CME formulations with 2% of 1,2-dimyristoyl-rac-glycerol-3-dodecaethylene glycol (GDM-12) in saline. The hashed line is (A:ip) and the solid line is (B:iv) The drug was administered intravenously or intraperitoneally and the dosing strength was 20 mg/kg.

The foregoing has been a description of certain non-limiting embodiments of the invention. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method for inhibiting cancer cell migration in a subject comprising administering to a subject in need thereof a pharmaceutical composition comprising a pharmaceutically acceptable carrier and a compound of formula I:

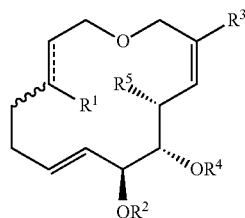

or a pharmaceutically acceptable salt thereof; wherein:
i. $R^1$ is hydrogen and ⚏ is a single bond; or
ii. $R^1$ is $C_{1-3}$ aliphatic optionally substituted with one or more halogens and ⚏ is a (Z)— double bond; and
$R^2$ is $C_{1-3}$ aliphatic;
$R^3$ and $R^5$ are each independently $C_{1-3}$ aliphatic; and
$R^4$ is -T-Y;
-T- is a $C_{1-3}$ bivalent saturated or unsaturated, straight or branched, hydrocarbon chain; and
—Y is selected from —$CO_2R$ or —C(O)N(R)$_2$; wherein
each R is independently —H or $C_{1-3}$ aliphatic.

2. The method of claim 1, wherein
i. ⚏ is a (Z)— double bond and $R^1$ is $C_{1-3}$ aliphatic substituted with one or more halogens; or
ii. $R^4$ is -T-Y wherein -T- is $CH_2$.

3. The method of claim 2, wherein
i. $R^1$ is —$CF_3$; or
ii. $R^4$ is -T-Y wherein -T- is $CH_2$ and —Y is —$CO_2H$.

4. The method of claim 1, wherein the compound is a compound of formula II:

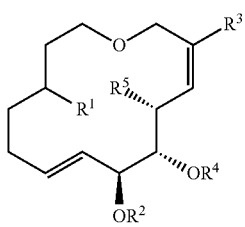

or a pharmaceutically acceptable salt thereof, wherein $R^1$ is hydrogen; or
a compound of formula III:

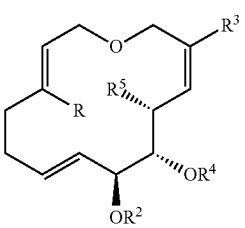

or a pharmaceutically acceptable salt thereof, wherein $R^1$ is $C_{1-3}$ aliphatic substituted with one or more halogens; or a compound of formula IV:

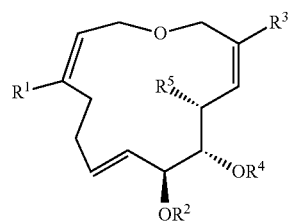

or a pharmaceutically acceptable salt thereof, wherein $R^1$ is $C_{1-3}$ aliphatic.

5. The method of claim 4, wherein the compound has the structure depicted below:

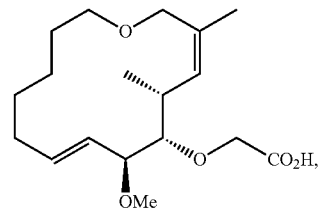 [SMILES: CO[C@H]1/C=C/CCCCCOC/C(C)=C\[C@@H](C)[C@@H]1OCC(=O)O]

or a pharmaceutically acceptable salt thereof.

6. The method of claim 4, wherein the compound has the structure depicted below:

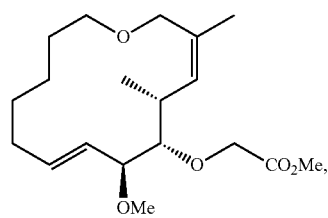 [SMILES: COC(=O)CO[C@H]1[C@H](C)/C=C(/C)COCCCCC/C=C/[C@@H]1OC]

or a pharmaceutically acceptable salt thereof.

7. The method of claim 4, wherein the compound has the structure depicted below:

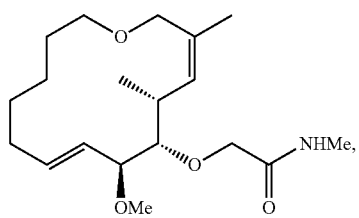 [SMILES: CNC(=O)CO[C@H]1[C@H](C)/C=C(/C)COCCCCC/C=C/[C@@H]1OC]

or a pharmaceutically acceptable salt thereof.

8. The method of claim 4, wherein the compound is a compound of formula III:

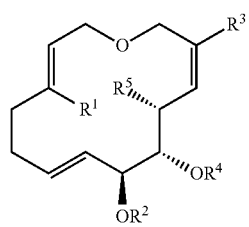

or a pharmaceutically acceptable salt thereof, wherein $R^1$ is —$CF_3$.

9. The method of claim 8, wherein the compound has the structure depicted below:

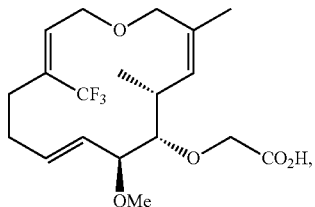 [SMILES: CO[C@H]1/C=C/CC/C(C(F)(F)F)=C/COC/C(C)=C\[C@@H](C)[C@@H]1OCC(=O)O]

or a pharmaceutically acceptable salt thereof.

10. The method of claim 4, wherein the compound is a compound of formula IV:

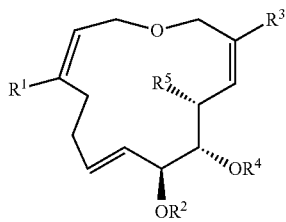

or a pharmaceutically acceptable salt thereof, wherein $R^1$ is methyl.

11. The method of claim 10, wherein the compound has the structure depicted below:

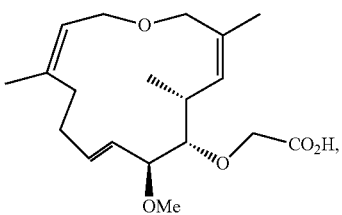 [SMILES: CO[C@H]1/C=C/CC/C(C)=C\COC/C(C)=C\[C@@H](C)[C@@H]1OCC(=O)O]

or a pharmaceutically acceptable salt thereof.

12. The method of claim 1, wherein the compound is a compound of formula II-a:

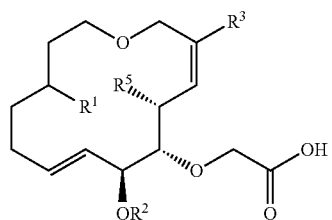

or a pharmaceutically acceptable salt thereof, wherein $R^1$ is hydrogen; or a compound of formula III-a:

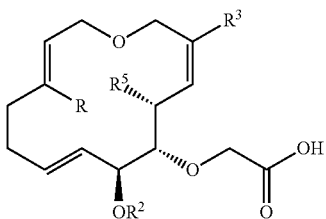

or a pharmaceutically acceptable salt thereof, wherein $R^1$ is $C_{1-3}$ aliphatic substituted with one or more halogens; or a compound of formula IV-a:

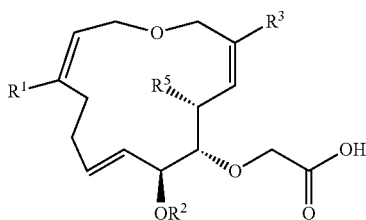

or a pharmaceutically acceptable salt thereof, wherein $R^1$ is $C_{1-3}$ aliphatic.

13. The method of claim 1, wherein $R^1$ is hydrogen $R^4$ is -T-Y wherein -T- is —$CH_2$—, and === is a single bond.

14. The method of claim 1, wherein $R^1$ is $C_{1-3}$ aliphatic substituted with one or more halogens, $R^4$ is -T-Y wherein -T- —$CH_2$—, and === is a (Z)— double bond.

15. The method of claim 14, wherein $R^1$ is —$CF_3$.

16. The method of claim 1, wherein $R^1$ is $C_{1-3}$ aliphatic $R^4$ is -T-Y wherein -T- —$CH_2$—, and === is a (Z)— double bond.

17. The method of claim 16, wherein $R^1$ is methyl.

18. The method of claim 1, wherein the compound is a compound selected from:

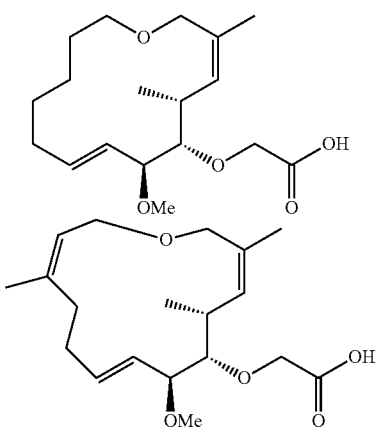

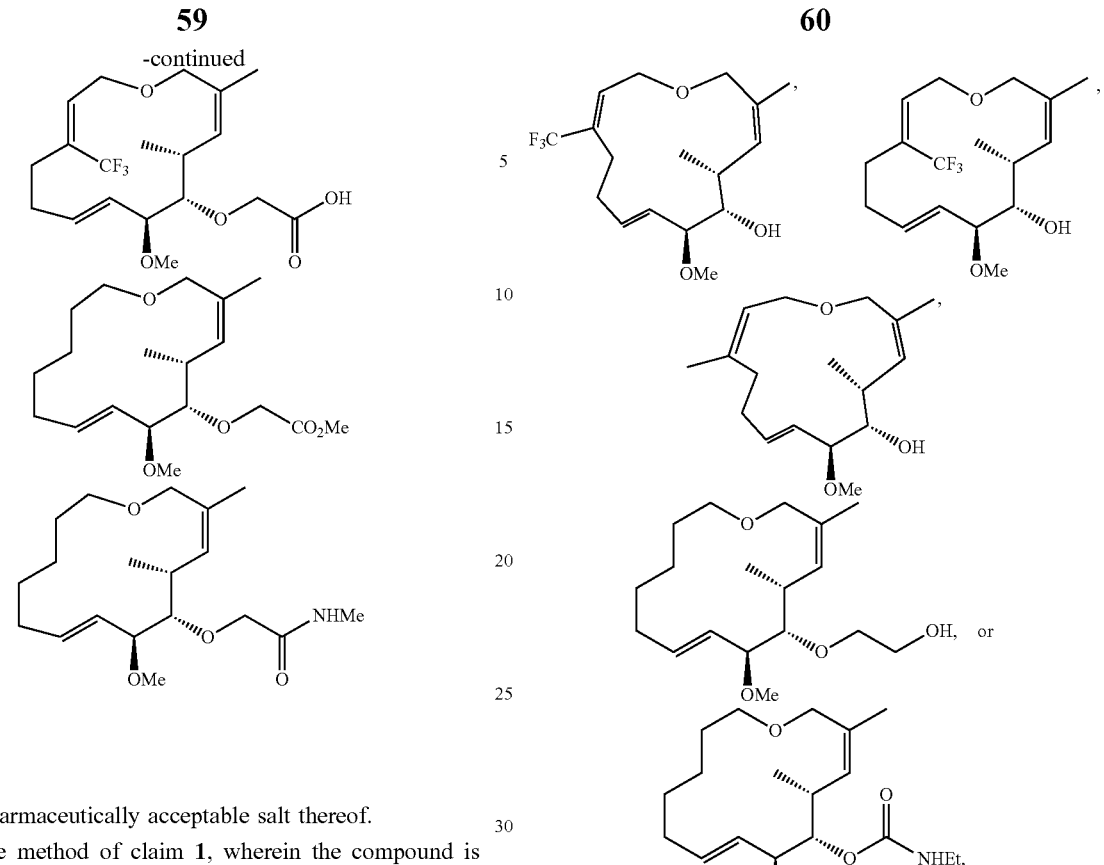

or a pharmaceutically acceptable salt thereof.

19. The method of claim 1, wherein the compound is present in an amount effective to inhibit or decrease metastatic spread of cancer.

20. The method of claim 1, wherein the cancer is breast cancer.

21. The method of claim 1, wherein the cancer is lung cancer.

22. The method of claim 1, wherein the cancer is multiple myeloma.

23. The method of claim 1, wherein the compound is present in an amount effective to inhibit migration of cancer cells from a primary breast tumor site to a secondary metastasis site.

24. The method of claim 1, wherein the cancer cell is in a solid tumor.

25. The method of claim 1, wherein the pharmaceutical composition is administered concurrently with, prior to, or subsequent to, one or more other desired therapeutics or medical procedures.

26. The method of claim 25, wherein the pharmaceutical composition further comprises a cytotoxic agent.

27. The method of claim 26, wherein the cytotoxic agent is an anticancer agent.

28. The method of claim 27, wherein the anticancer agent is 12,13-desoxyepothilone B, (E)-9,10-dehydro-12,13-desoxyEpoB, 26-CF3-(E)-9,10-dehydro-12,13-desoxyEpoB, taxol, radicicol, or TMC-95A/B.

29. The method of claim 27, further comprising a palliative agent.

30. A method for inhibiting cancer cell migration in a subject comprising administering to a subject in need thereof a pharmaceutical composition comprising a pharmaceutically acceptable carrier and a compound selected from:

or a pharmaceutically acceptable salt thereof.

31. A method for treating or lessening the severity of cancer in a subject suffering therefrom comprising administering to a subject in need thereof a pharmaceutical composition comprising a pharmaceutically acceptable carrier and a compound of formula I:

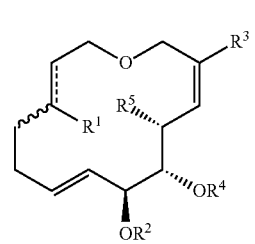

or a pharmaceutically acceptable salt thereof; wherein:
i. $R^1$ is hydrogen and ═══ is a single bond; or
ii. $R^1$ is $C_{1-3}$ aliphatic optionally substituted with one or more halogens and ═══ is a (Z)— double bond; and
$R^2$ is $C_{1-3}$ aliphatic;
$R^3$ and $R^5$ are each independently $C_{1-3}$ aliphatic; and
$R^4$ is -T-Y;
-T- is a $C_{1-3}$ bivalent saturated or unsaturated, straight or branched, hydrocarbon chain; and
—Y is selected from —$CO_2R$ or —$C(O)N(R)_2$;
wherein
each R is independently —H or $C_{1-3}$ aliphatic.

32. The method of claim 31, wherein the cancer is breast cancer.

33. The method of claim 31, wherein the cancer is lung cancer.

34. The method of claim 31, wherein the cancer is multiple myeloma.

35. The method of claim 31, wherein the compound is a compound selected from:

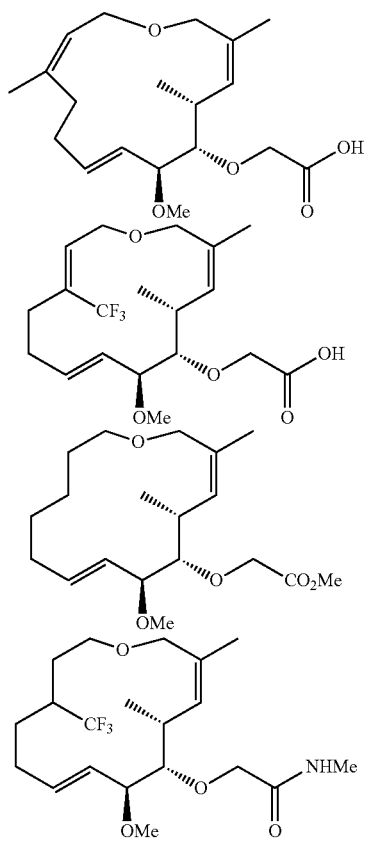

or a pharmaceutically acceptable salt thereof.

36. The method of claim 35, wherein the cancer is breast cancer.

37. The method of claim 35, wherein the cancer is lung cancer.

38. The method of claim 35, wherein the cancer is multiple myeloma.

39. The method according to claim 36, wherein the compound has the structure depicted below:

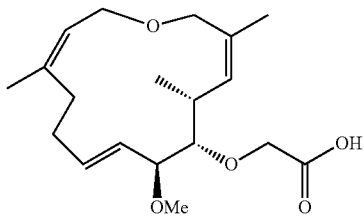 [SMILES: CO[C@H]1/C=C/CC/C(C)=C\COC/C(C)=C\[C@@H](C)[C@@H]1OCC(=O)O]

or a pharmaceutically acceptable salt thereof.

40. The method according to claim 37, wherein the compound has the structure depicted below:

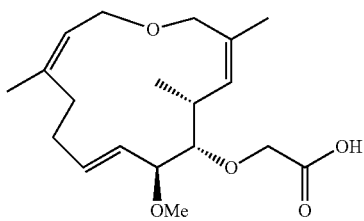 [SMILES: CO[C@H]1/C=C/CC/C(C)=C\COC/C(C)=C\[C@@H](C)[C@@H]1OCC(=O)O]

or a pharmaceutically acceptable salt thereof.

41. The method according to claim 38, wherein the compound has the structure depicted below:

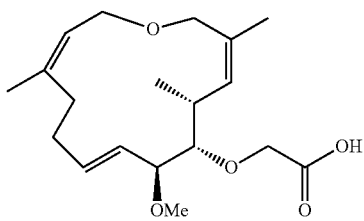 [SMILES: CO[C@H]1/C=C/CC/C(C)=C\COC/C(C)=C\[C@@H](C)[C@@H]1OCC(=O)O]

or a pharmaceutically acceptable salt thereof.

* * * * *

UNITED STATES PATENT AND TRADEMARK OFFICE
CERTIFICATE OF CORRECTION

PATENT NO. : 9,546,146 B2  
APPLICATION NO. : 15/065090  
DATED : January 17, 2017  
INVENTOR(S) : Danishefsky et al.

It is certified that error appears in the above-identified patent and that said Letters Patent is hereby corrected as shown below:

In the Specification

In Column 1, beginning at Line 20 please delete:
"This invention was made with government support under grant CA103823 awarded by the National Institutes of Health. The government has certain rights in the invention."

And insert:
-- This invention was made with government support under grants CA103823 and AI016943 awarded by the National Institutes of Health. The government has certain rights in the invention. --

Signed and Sealed this
Twenty-third Day of May, 2017

Michelle K. Lee
*Director of the United States Patent and Trademark Office*